US012208013B2

(12) United States Patent
Schwartz et al.

(10) Patent No.: US 12,208,013 B2
(45) Date of Patent: Jan. 28, 2025

(54) IMPLANT SYSTEMS FOR REPAIR OF A HUMERAL HEAD

(71) Applicant: BIOPOLY, LLC, Fort Wayne, IN (US)

(72) Inventors: Herbert E. Schwartz, Fort Wayne, IN (US); Matthew L. Mroczkowski, Fort Wayne, IN (US)

(73) Assignee: BioPoly, LLC, Fort Wayne, IN (US)

( * ) Notice: Subject to any disclaimer, the term of this patent is extended or adjusted under 35 U.S.C. 154(b) by 312 days.

(21) Appl. No.: 17/375,701

(22) Filed: Jul. 14, 2021

(65) Prior Publication Data

US 2021/0338443 A1 Nov. 4, 2021

Related U.S. Application Data

(63) Continuation of application No. PCT/US2020/013482, filed on Jan. 14, 2020.
(Continued)

(51) Int. Cl.
*A61F 2/24* (2006.01)
*A61B 17/17* (2006.01)
(Continued)

(52) U.S. Cl.
CPC ........ *A61F 2/4003* (2013.01); *A61B 17/1778* (2016.11); *A61F 2/30734* (2013.01);
(Continued)

(58) Field of Classification Search
None
See application file for complete search history.

(56) References Cited

U.S. PATENT DOCUMENTS 6,383,224 B1 * 5/2002 Gie ............... A61F 2/30734
623/22.39
6,629,997 B2 * 10/2003 Mansmann ....... A61F 2/30965
623/14.12
(Continued)

FOREIGN PATENT DOCUMENTS

WO   WO-2007078978 A2 *   7/2007   ......... A61B 17/0401
WO   WO-2016151047 A1 *   9/2016   ......... A61F 2/30749
(Continued)

OTHER PUBLICATIONS

International Preliminary Report on Patentability for International Application No. PCT/US2020/013482, dated Jun. 16, 2021, 9 pages, International Bureau of WIPO.
(Continued)

*Primary Examiner* — Ann Schillinger
(74) *Attorney, Agent, or Firm* — Heslin Rothenberg Farley & Mesiti P.C.

(57) ABSTRACT

A humeral implant system, for example, includes an implant and a cutting guide system. The implant is a spherical wedge having an elongated curved upper surface having a first edge and a spaced apart second edge, a first surface having a curved upper edge joined to the first edge of the elongated curved upper surface, and a second surface having a curved upper edge joined to the second edge of the elongated curved upper surface. A lower edge of the first surface is joined to a lower edge of the second surface. The first surface and the second surface are disposed at an angle. The cutting system has a body having a first guide and a second guide for resecting a cutout in a humeral head, in which the cutout has a first surface and a second surface corresponding to the first surface and the second surface of the implant.

30 Claims, 31 Drawing Sheets

Related U.S. Application Data

(60) Provisional application No. 62/792,594, filed on Jan. 15, 2019.

(51) Int. Cl.
| | |
|---|---|
| *A61F 2/30* | (2006.01) |
| *A61F 2/40* | (2006.01) |
| *A61F 2/44* | (2006.01) |
| *A61F 2/46* | (2006.01) |
| *A61F 2/88* | (2006.01) |
| *A61F 2/91* | (2013.01) |

(52) U.S. Cl.
CPC ........ *A61F 2/30767* (2013.01); *A61F 2/4612* (2013.01); *A61F 2/4684* (2013.01); *A61F 2002/30242* (2013.01); *A61F 2002/30616* (2013.01); *A61F 2002/30736* (2013.01); *A61F 2002/3092* (2013.01); *A61F 2002/4007* (2013.01); *A61F 2002/4687* (2013.01)

(56) References Cited

U.S. PATENT DOCUMENTS

| | | | | |
|---|---|---|---|---|
| 6,696,073 | B2* | 2/2004 | Boyce | A61L 31/005 424/443 |
| 6,855,167 | B2* | 2/2005 | Shimp | A61F 2/28 623/17.11 |
| 7,060,096 | B1 | 6/2006 | Schopf et al. | |
| 7,618,454 | B2* | 11/2009 | Bentley | A61F 2/4455 623/17.11 |
| 7,662,954 | B2* | 2/2010 | James | B29C 67/24 536/55.1 |
| 8,002,840 | B2* | 8/2011 | Aram | A61B 17/155 623/20.15 |
| 8,303,967 | B2 | 11/2012 | Clineff et al. | |
| 8,506,569 | B2* | 8/2013 | Keefer | A61B 17/1778 606/177 |
| 8,702,717 | B2 | 4/2014 | Rauscher et al. | |
| 9,278,004 | B2* | 3/2016 | Shenoy | A61B 17/8872 |
| 9,795,410 | B2* | 10/2017 | Shenoy | A61B 17/56 |
| 10,045,851 | B2* | 8/2018 | Grotz | A61L 27/56 |
| 10,350,078 | B2* | 7/2019 | Ek | A61F 2/30734 |
| 10,449,054 | B2* | 10/2019 | Hopkins | A61B 17/8605 |
| 10,980,640 | B2* | 4/2021 | Chavarria | A61F 2/4612 |
| 11,285,009 | B2* | 3/2022 | Terrill | A61F 2/30771 |
| 11,896,476 | B2* | 2/2024 | Shulock | A61B 17/56 |
| 2003/0009235 | A1* | 1/2003 | Manrique | B29C 41/22 623/23.51 |
| 2003/0158605 | A1 | 8/2003 | Tornier | |
| 2004/0148026 | A1* | 7/2004 | Bonutti | A61F 2/4455 623/16.11 |
| 2004/0267366 | A1* | 12/2004 | Kruger | A61F 2/4455 623/17.11 |
| 2005/0049710 | A1* | 3/2005 | O'Driscoll | A61F 2/3804 623/20.11 |
| 2005/0182493 | A1 | 8/2005 | Bertram, III | |
| 2006/0074430 | A1 | 4/2006 | Deffenbaugh et al. | |
| 2008/0188945 | A1* | 8/2008 | Boyce | A61B 17/0401 623/23.61 |
| 2010/0268339 | A1* | 10/2010 | Malinin | A61F 2/447 623/17.11 |
| 2011/0009964 | A1 | 1/2011 | Schwartz et al. | |
| 2011/0264153 | A1 | 10/2011 | Hassler et al. | |
| 2012/0053590 | A1* | 3/2012 | Allen | A61F 2/34 606/87 |
| 2012/0283840 | A1* | 11/2012 | Frederick | A61F 2/4657 623/22.32 |
| 2013/0184820 | A1* | 7/2013 | Schwartz | A61F 2/4684 623/14.12 |
| 2013/0211531 | A1* | 8/2013 | Steines | A61F 2/3859 623/20.14 |
| 2013/0238099 | A1 | 9/2013 | Hardy et al. | |
| 2014/0257304 | A1 | 9/2014 | Eash | |
| 2015/0157462 | A1 | 6/2015 | Ek et al. | |
| 2017/0027708 | A1 | 2/2017 | Shenoy | |
| 2017/0224496 | A1* | 8/2017 | Witt | A61F 2/3603 |
| 2018/0028202 | A1 | 2/2018 | Nelson et al. | |
| 2021/0338445 | A1* | 11/2021 | Schwartz | A61B 17/1778 |

FOREIGN PATENT DOCUMENTS

| | | |
|---|---|---|
| WO | 2020150216 A1 | 7/2020 |
| WO | 2020150217 A1 | 7/2020 |

OTHER PUBLICATIONS

International Search Report and Written Opinion of the International Searching Authority for International Patent Application No. PCT/US2020/013482 mailed on Mar. 19, 2020.

International Search Report and Written Opinion of the International Searching Authority for International Patent Application No. PCT/US2020/013484 mailed on Apr. 6, 2020.

Schwartz et al., U.S. Appl. No. 17/375,705, filed Jul. 14, 2021, entitled "Implant Systems For Repair Of A Glenoid Cavity".

* cited by examiner

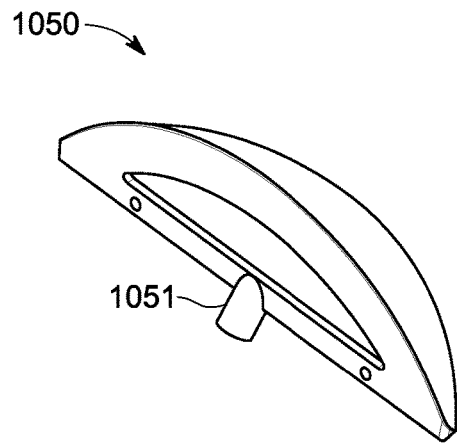
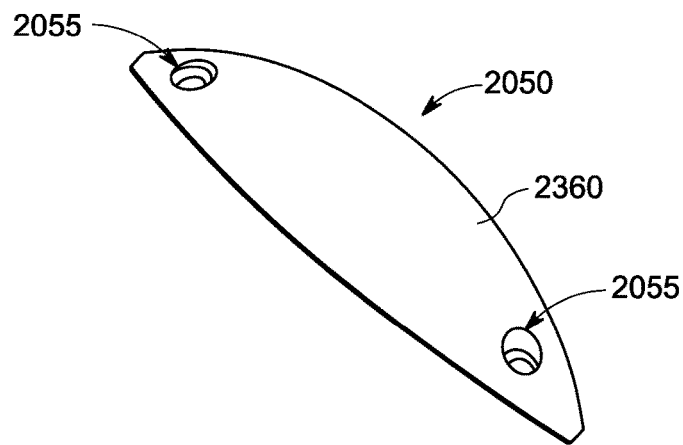
FIG. 27  FIG. 28
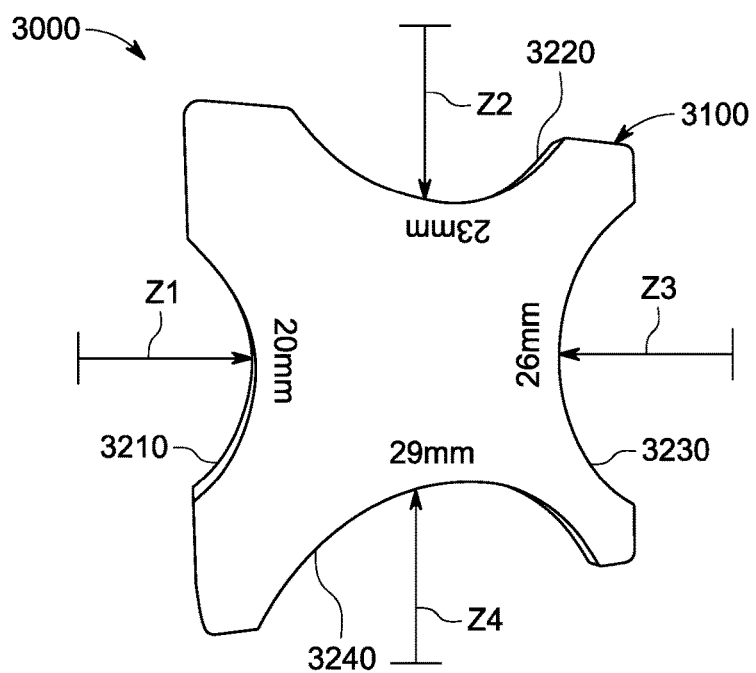
FIG. 29

IMPLANT SYSTEMS FOR REPAIR OF A HUMERAL HEAD

CLAIM TO PRIORITY APPLICATION

This application is a U.S. National Stage Continuation Application based on International Application No. PCT/US2020/013482 filed on Jan. 14, 2020, and claims the priority to U.S. Provisional Application No. 62/792,594 filed on Jan. 15, 2019, entitled "Implant Systems For Repair Of A Humeral Head", which is hereby incorporated herein by reference in its entirety.

CROSS-REFERENCE TO RELATED APPLICATION

This application is related to commonly assigned, co-filed International Application No. PCT/US2020/013484, filed Jan. 14, 2020, entitled "Implant Systems for Repair of a Glenoid Cavity", which international PCT patent application claims priority to U.S. provisional patent application No. 62/792,618, filed Jan. 15, 2019, entitled "Implant Systems for Repair of a Glenoid Cavity", which applications are hereby incorporated herein by reference in their entirety.

FIELD OF THE DISCLOSURE

The present disclosure relates generally to surgical implants for use in repairing a shoulder joint, and more particularly to implant systems having an implant or implant apparatus and a corresponding cutting guide system for repair of a humeral head.

BACKGROUND

Hill-Sachs lesions, in the head of a humerus, can be treated with different techniques including remplissage, humeral head reconstruction with allograft, partial humeral head arthroplasty, or hemiarthroplasty.

SUMMARY

Shortcomings of the prior art are overcome and additional advantages are provided through the provision, in one embodiment, of a humeral implant system, for example, having an implant and a cutting guide system. The implant is a spherical wedge having an elongated curved upper surface with a first edge and a spaced apart second edge, a first surface having a curved upper edge joined to the first edge of the elongated curved upper surface, and a second surface having a curved upper edge joined to the second edge of the elongated curved upper surface. A lower edge of the first surface is joined to a lower edge of the second surface. The first surface and the second surface are disposed at an angle. The cutting guide system has a body with a first guide and a second guide for resecting a cutout in a humeral head, in which the cutout has a first surface and a second surface corresponding to the first surface and the second surface of the implant.

In another embodiment, a humeral implant includes, for example, a spherical wedge formed from a metal and or polymeric material and having an elongated curved upper surface with a first edge and a spaced apart second edge, a first surface having a curved upper edge joined to the first edge of the elongated curved upper surface, and a second surface having a curved upper edge joined to the second edge of the elongated curved upper surface. A lower edge of the first surface is joined to a lower edge of the second surface. The first surface and the second surface are disposed at an angle.

In another embodiment, a humeral implant cutting guide system includes, for example, a body defining a frame having an opening extending therethrough, a plurality of through-holes extending through the frame for receiving pins for use in securing the body to a humeral head, and the opening defining a first guide and a second guide for resecting a cutout in the humeral head, the cutout having a first surface and a second surface corresponding to a first surface and a second surface of the humeral implant.

In another embodiment, a method includes, for example, using a cutting guide to form a cutout in a humeral head around a depression having a first configuration, the cutout in the humeral head having a second configuration conforming to a predetermined humeral implant, securing the predetermined humeral implant in the cutout in the humeral head, and wherein an outer surface of the humeral implant corresponds to the surface anatomy of the humeral head around the cutout.

BRIEF DESCRIPTION OF THE DRAWINGS

The subject matter which is regarded as the disclosure is particularly pointed out and distinctly claimed in the concluding portion of the specification. The disclosure, however, may best be understood by reference to the following detailed description of various embodiments and the accompanying drawings in which:

FIG. 27 is a perspective view of the implant of FIG. 26, according to an embodiment of the present disclosure;

FIG. 28 is a perspective view an implant, according to an embodiment of the present disclosure;

FIG. 29 is a perspective view of a tool for measuring the radius of a humeral head, according to an embodiment of the present disclosure;

DETAILED DESCRIPTION

Generally stated, disclosed herein are implants, implant apparatus, and implant cutting guide system. Implant systems may include one or more implants or implant apparatuses along with a corresponding implant cutting guide system. Further, surgical methods employing the same are also disclosed.

In this detailed description and the following claims, the words proximal, distal, anterior, posterior, medial, lateral, superior, and inferior are defined by their standard usage for indicating a particular part of a bone or implant according to the relative disposition of the natural bone or directional terms of reference.

Positions or directions may be used herein with reference to anatomical structures or surfaces. For example, as the current devices and methods are described herein with reference to use with the bones of the shoulder, the bones of the shoulder may be used to describe the surfaces, positions, directions or orientations of the implant apparatus, implant installation apparatus, and surgical methods. Further, the devices and surgical methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the device and surgical methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the apparatus and surgical methods, and the aspects, components, features and the like thereof, described herein with respect to a left shoulder may be mirrored so that they likewise function with a right shoulder and vice versa.

Figure 1:
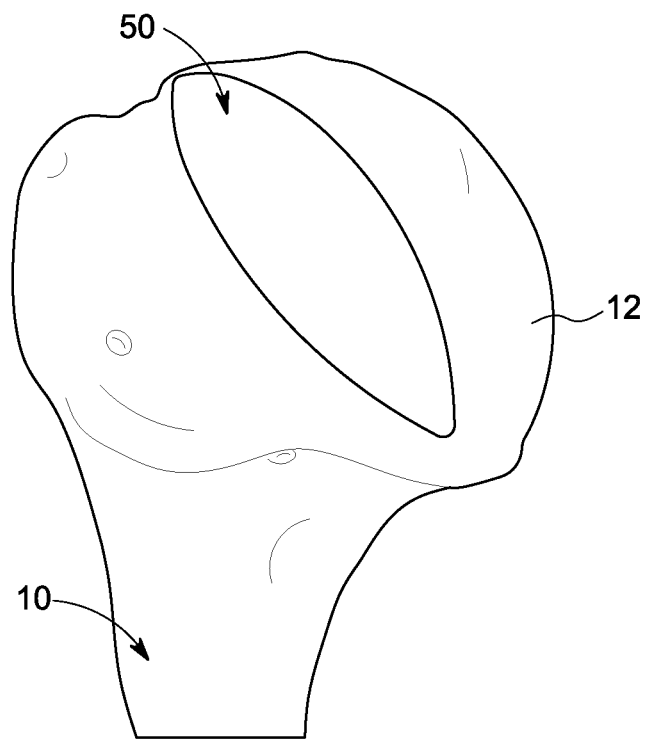
FIG. 1 is a perspective view of an implant apparatus secured to a humeral head, according to an embodiment of the present disclosure.
Figure 2:
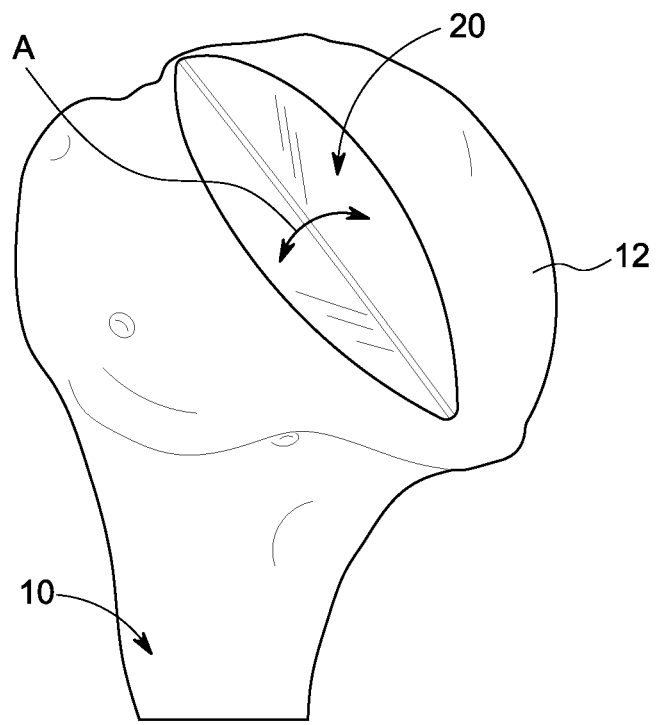
FIG. 2 is a perspective view of the humeral head of FIG. 1 with the implant apparatus removed illustrating a cutout in the humeral head, according to an embodiment of the present disclosure.
Figure 3:
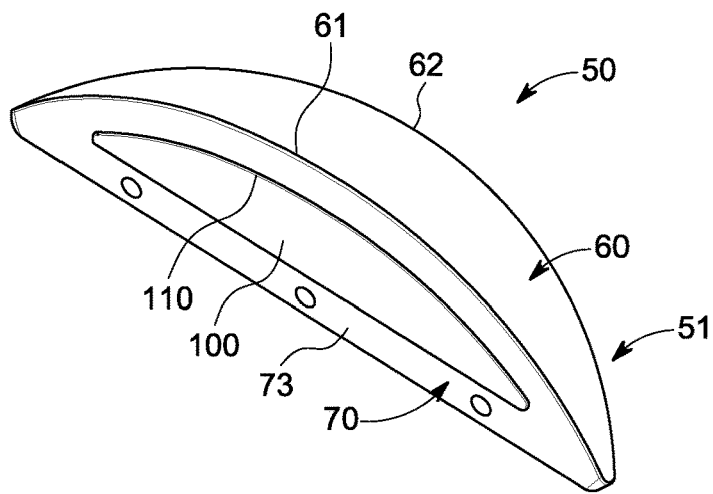
FIG. 3 is a perspective view of the implant apparatus of FIG. 1, according to an embodiment of the present disclosure.
Figure 16:
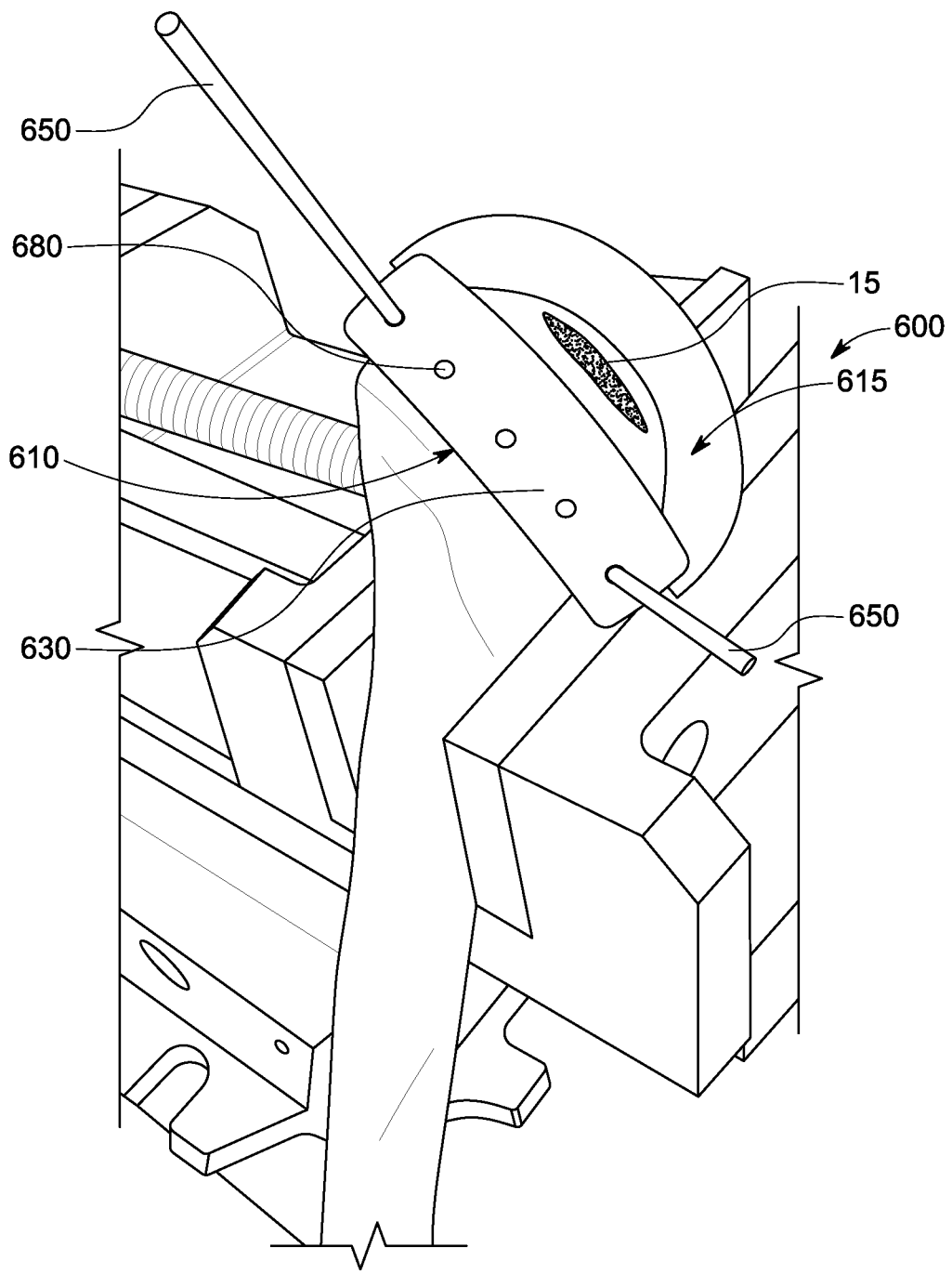
FIG. 16 is a perspective view of a cutting guide system secured to the humeral head prior to cutting the humeral head, according to an embodiment of the present disclosure.
Figure 17:
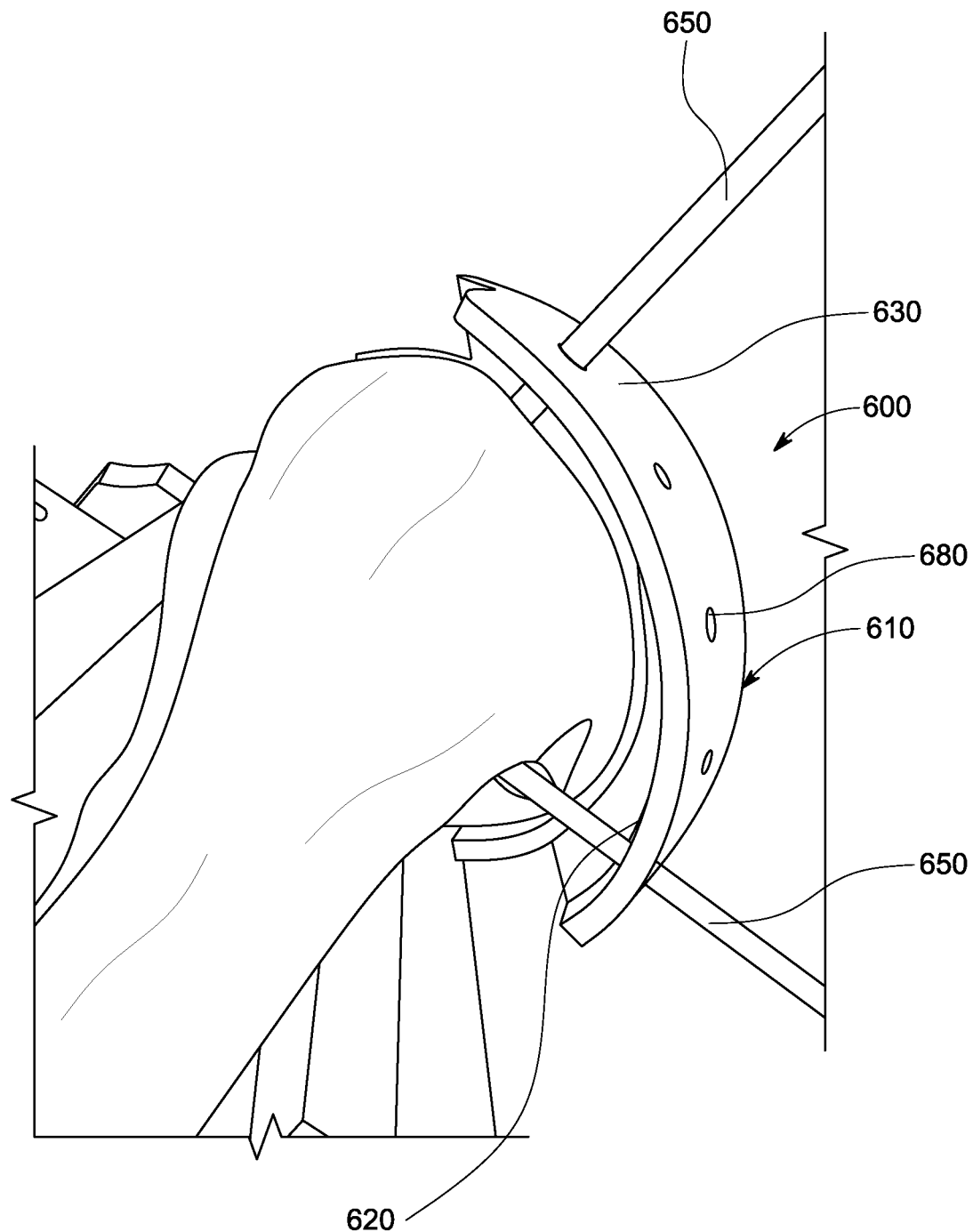
FIG. 17 is another perspective view of the cutting guide system of FIG. 16 secured to the humeral head prior to cutting the humeral head, according to an embodiment of the present disclosure.
Figure 18:
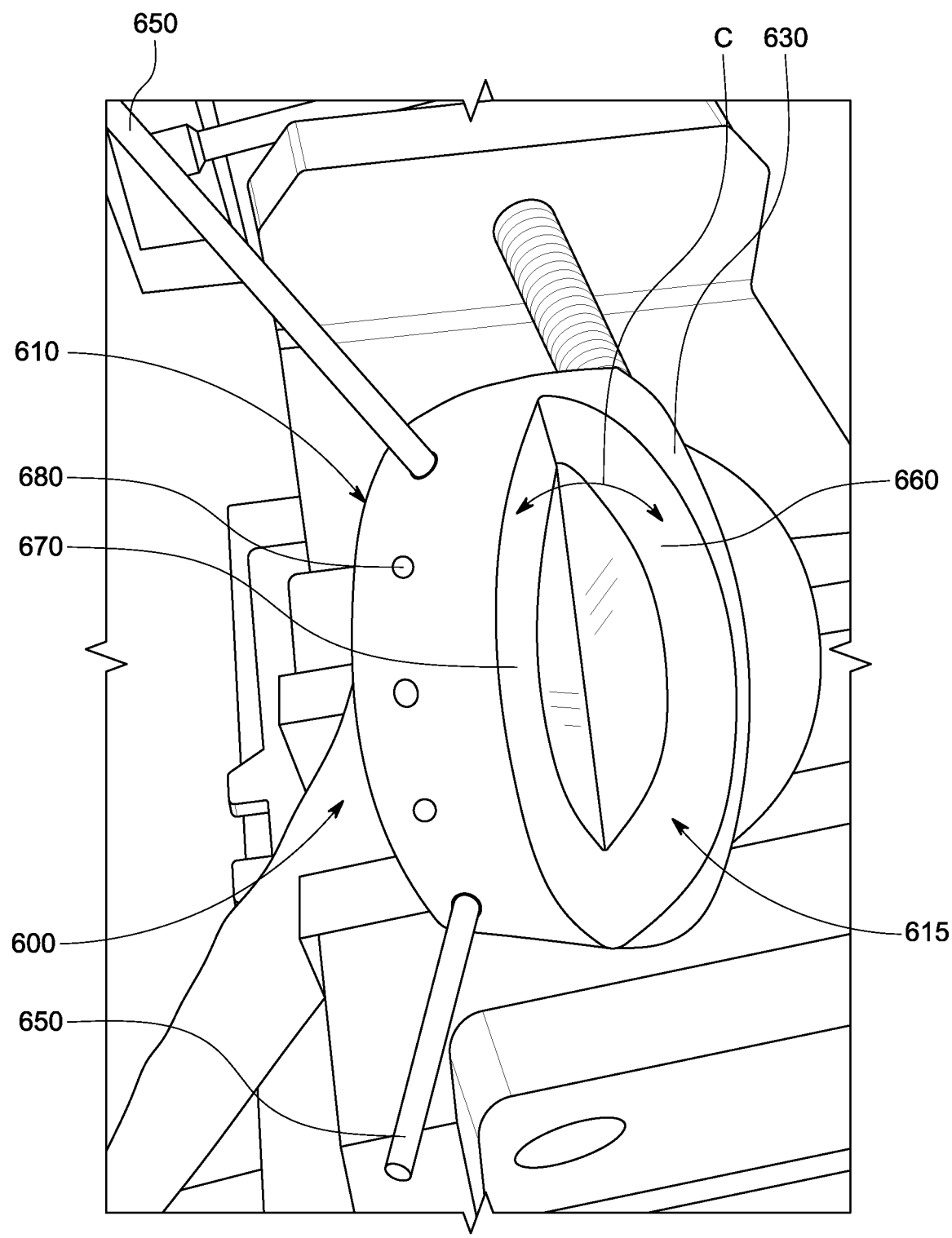
FIG. 18 is a perspective view of the cutting guide system secured to the humeral head after forming a cutout in the humeral head, according to an embodiment of the present disclosure.
Figure 26:
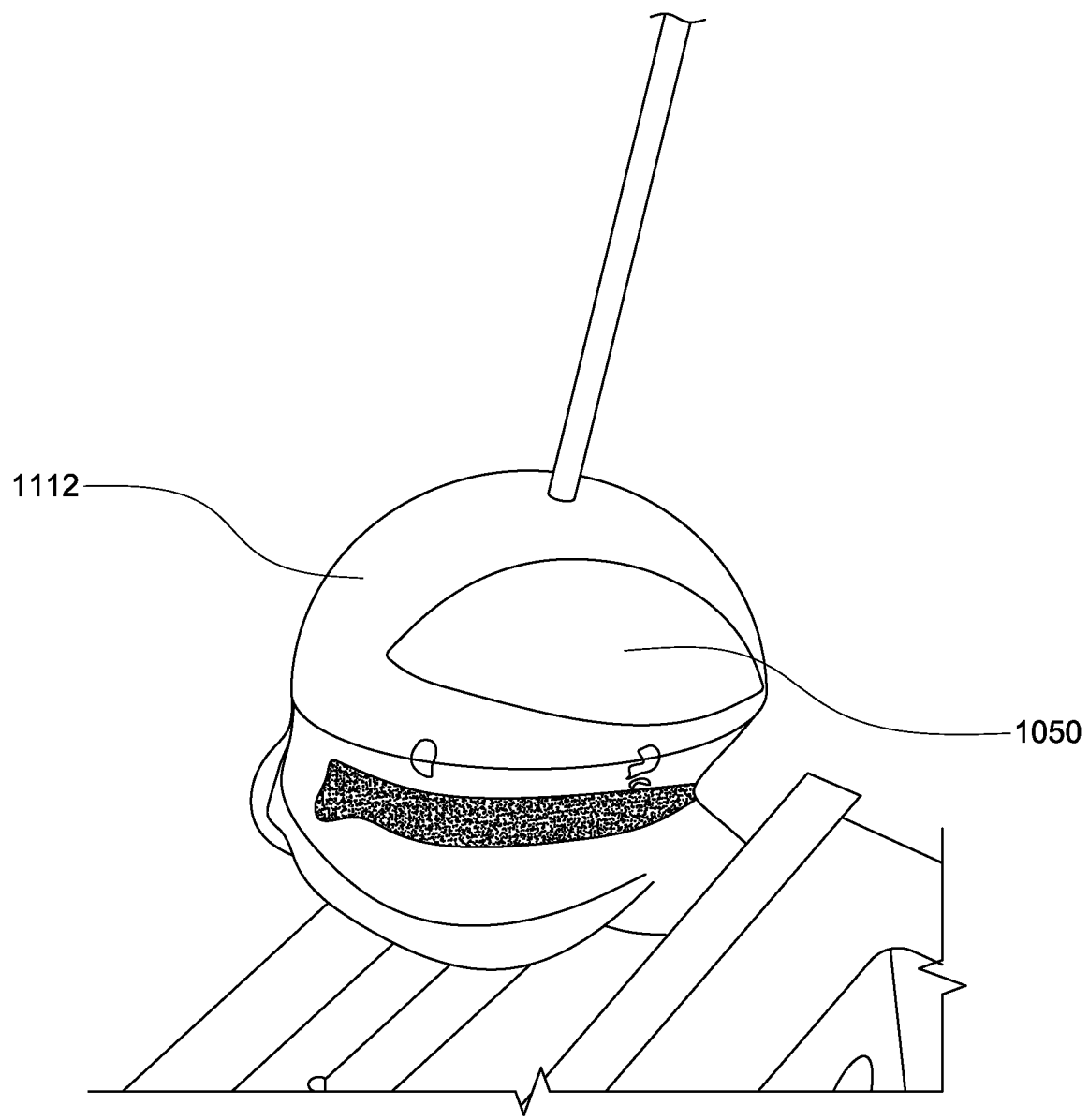
FIG. 26 is a perspective view of an implant secured in the cutout of the humeral head of FIG. 25, according to an embodiment of the present disclosure.
Figure 34:
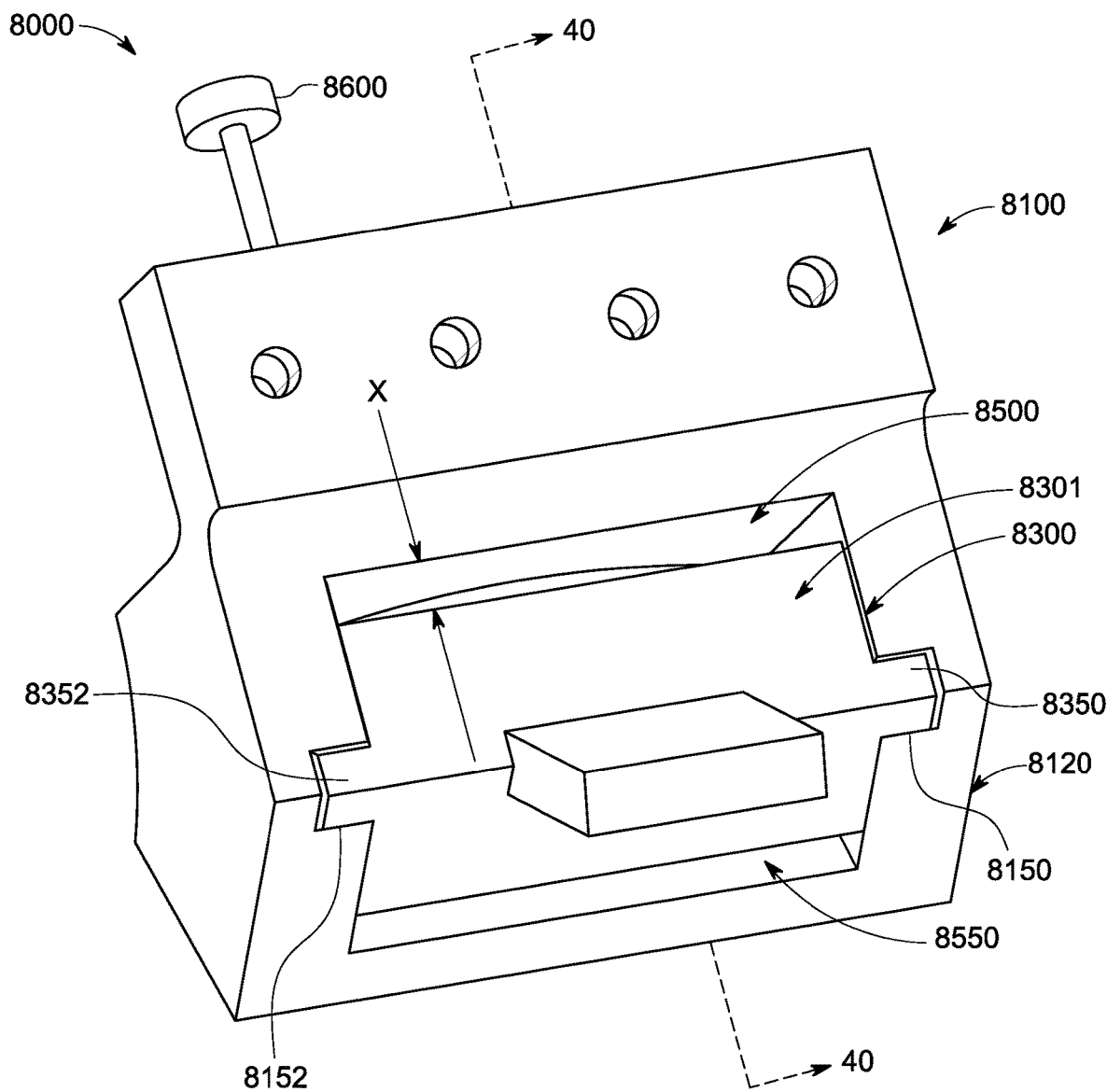
FIG. 34 is a perspective view of a cutting guide system, according to an embodiment of the present disclosure.

Referring to the drawings, wherein like reference numerals are used to indicate like or analogous components throughout the several views, and with particular reference to FIGS. 1 and 2, there is illustrated an exemplary embodiment of a biocompatible implant apparatus 50 (FIG. 1) installed in a cutout 20 (FIG. 2) in a head 12 of a humerus 10 such as for the repair of a Hill-Sachs lesion (not shown). Implant apparatus 50 is designed to restore the normal anatomy of the humeral head in the posterolateral area where a Hill-Sachs lesion occurs. With reference to FIGS. 16-18, a cutting guide system 600 allows resecting a cutout around a Hill-Sachs lesion (FIG. 16) sized for receiving the implant apparatus 50 (FIG. 1). FIGS. 19-23 illustrate a drill guide 700 (FIG. 19) and a cutting guide system 900 (FIG. 22) that allows for resecting a corresponding cutout around a Hill-Sachs lesion 115 (FIG. 21) that is sized for receiving an implant apparatus 1050 (FIG. 26). FIG. 34 illustrates a cutting guide system 8000 having a support portion 8100 and an insert portion 8300 for resecting a cutout, for example, around a Hill-Sachs lesion sized for receiving an implant or implant apparatus. As further described below, implant systems having an implant or implant apparatus and a cutting guide system of the present disclosure may be designed to fit the various sized patient anatomies that may be encountered. For example, the implants, implant apparatus, cutting guide systems and may be designed in multiple radii of curvature, width, and depth options to allow for selecting the best fit for a given patient bone anatomy and corresponding defect.

The implants and implant apparatus can also be used in the less common "reverse" Hill-Sachs lesion which is on the anterior side of the humeral head. The implants and implant apparatus for a Hill-Sachs lesion can be used as a hemi-arthroplasty or in conjunction with a glenoid implant apparatus. For example, the present disclosure for the implants and implant apparatus for repair of the humeral head may be used in conjunction with the glenoid implant apparatus for the repair of a Bankart lesion described in the commonly assigned, co-filed, international PCT patent application no. PCT/US2020/013484, filed Jan. 14, 2020, entitled "Implant Systems for Repair of a Glenoid Cavity", which international PCT patent application claims priority to U.S. provisional patent application No. 62/792,618, filed Jan. 15, 2019, entitled "Implant Systems For Repair Of A Glenoid", which applications are hereby incorporated herein by reference in their entirety.

As will be appreciated from the present description, the present disclosure addresses the problem of recurring instability and dislocation events caused by, for example, the presence of a lesion on the humeral head (Hill-Sachs lesion) resulting from a traumatic injury (shoulder dislocation). The present disclosure provides a solution to surgeons for the treatment of patients with debilitating instability of the shoulder joint by providing an implantable device or apparatus that correctly replicates the normal anatomy of the affected bone in the shoulder, re-creating the original articular surface geometry. Advantages of the present disclosure may be shorter surgery time compared to conventional humeral head reconstruction with an allograft as there is, for example, no need for a surgeon to prepare an allograft, and minimal bone resection as the implant is specifically designed for the lesion being repaired. From the present disclosure, it will be appreciated that the implants, implant apparatus, and cutting guides may be suitably employed in connection with other bones of a patient.

As shown in FIGS. 1 and 3-6, the implant apparatus 50 is designed in a unique spherical wedge shape of a portion of a sphere such as similar to a section of an orange or an irregular spherical wedge shape configuration. This configuration also corresponds to the Hill-Sachs lesion geometry. With reference to FIGS. 3-7, the implant apparatus 50 may include a body 51, a first porous material layer 100, and a second porous material layer 200.

Figure 4:
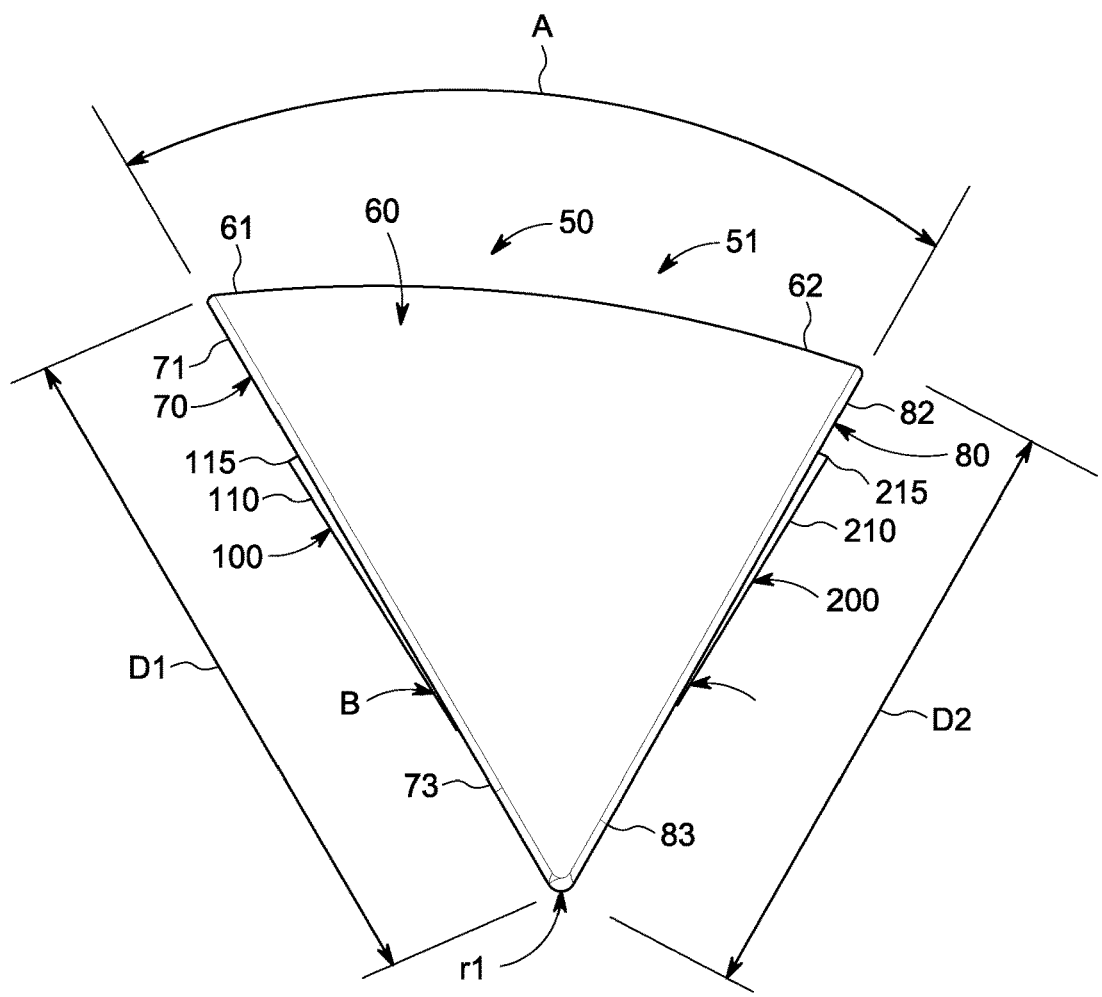
FIG. 4 is an enlarged end view of the implant apparatus of FIG. 3, according to an embodiment of the present disclosure.
Figure 5:
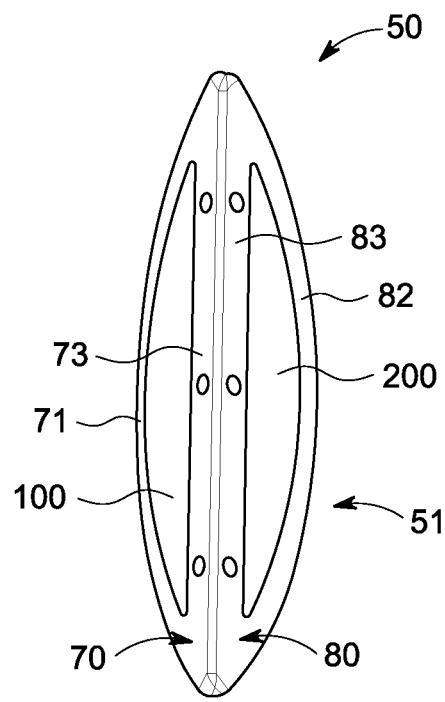
FIG. 5 is a bottom view of the implant apparatus of FIG. 3, according to an embodiment of the present disclosure.
Figure 6:
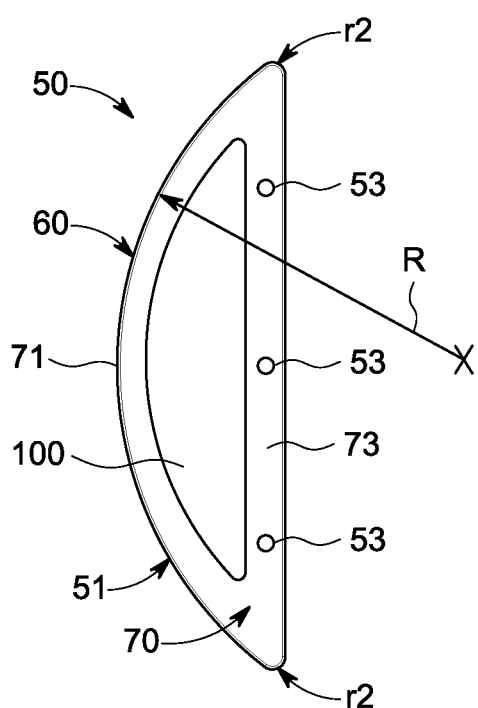
FIG. 6 is a first side view of the implant apparatus of FIG. 3, according to an embodiment of the present disclosure.

The implant apparatus 50 may include the body 51 having a curved outer (articulating) surface 60, a first surface 70, and a second surface 80. The curved surface 60 may be a generally convex surface that provides an articulating surface against a corresponding glenoid surface. The curved surface 60 may be a constant radial surface, for example, an outer portion of a sphere, or may be a non-constant curved surface. The curved surface 60 includes a first curved edge 61 joined to an upper curved edge 71 of first surface 70. The curved surface 60 includes a second curved edge 62 joined to an upper curved edge 82 of the second surface 80. A lower straight edge 73 of the first surface 70 may be joined to a lower straight edge 83 of the second surface 80. The lower straight edges 73 and 83 may be rounded and have a radius r1 (FIG. 4). The ends of straight edges 73 and 83 may be rounded and have a radius r2 (FIGS. 5 and 6). The first surface 70 may be disposed at a constant angle A (FIG. 4) relative to the second surface 80. In other embodiments, a first surface and a second surface may be disposed at other orientations or varying orientations and/or have other configurations other than planar surfaces. For example, the implant body 51 may include curved surface 60 having a radius R (FIG. 6), the first surface 70 having a depth D1, and second surface 80 having a depth D2. The depths may be differently sized, for example as shown in FIG. 4, resulting in an irregular wedge shape. In other embodiments, the depths may be the same.

FIGS. 8-11 illustrate the body 51 of the implant apparatus 50 (FIGS. 3-7). The first surface 70 of body 51 may include a first recess or relief 75 disposed generally in the center of first surface 70. The second surface 80 of body 51 may include a second recess or relief 85 disposed generally in the center of the second surface 80. The first surface 70 may define a first flat surface disposed around relief 75. The second surface 80 may define a second flat surface disposed around second relief 85.

Figure 9:
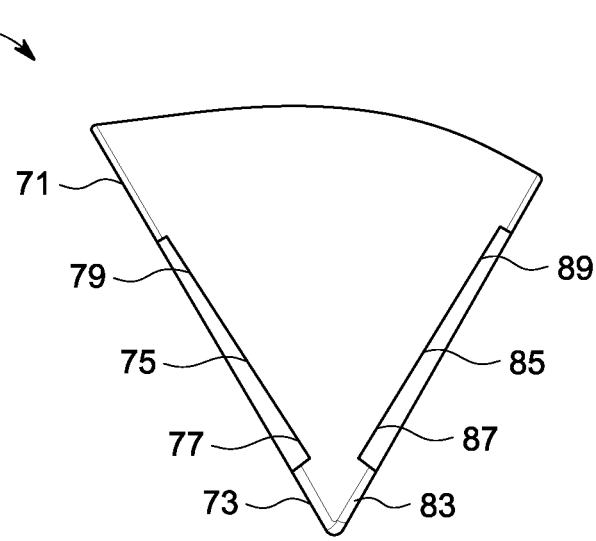
FIG. 9 is a cross-sectional view of the implant body taken along line 9-9 in FIG. 8, according to an embodiment of the present disclosure.
Figure 10:
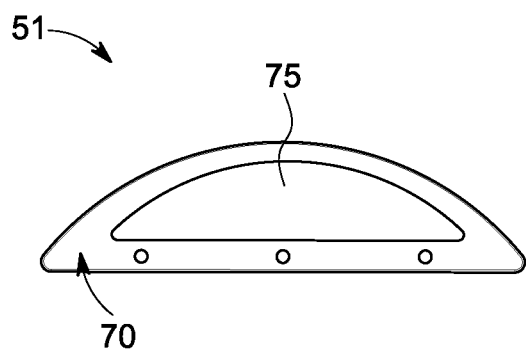
FIG. 10 is a first side of the implant body of FIG. 8, according to an embodiment of the present disclosure.
Figure 11:
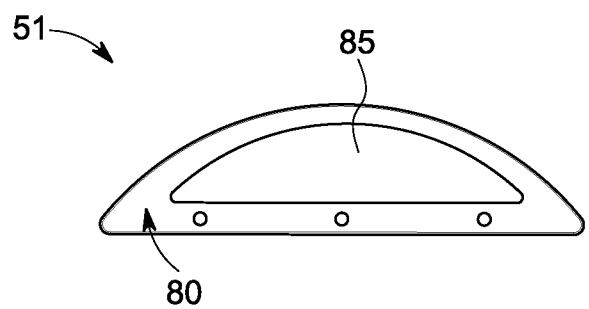
FIG. 11 is a second side of the implant body of FIG. 8, according to an embodiment of the present disclosure.

As best shown in FIG. 9, the reliefs 75 and 85 may be tapered reliefs that extend into first surface 70 and second surface 80, respectively. For example, the first relief 75 may include an inner portion 77 disposed at a deeper level or depth relative to first surface 70 adjacent to the straight edge 73 compared to an outer portion 79 disposed at a shallower level or depth relative to first surface 70 adjacent to the curved edge 71. The second relief 85 may include an inner portion 87 disposed at a deeper level or depth relative to the second surface 80 adjacent to the straight edge 83 compared to an upper portion 89 disposed at a shallower level or depth relative to second surface 80 adjacent to the curved edge 82. Reliefs 75 and 85 may have generally arcuate shapes. In other embodiments, the reliefs may have other suitable shapes and configurations. The depth of the recesses adjacent to the straight edge may be between about 0.5 millimeters and about 2.0 millimeters (mm) or about 0.75 millimeter (mm), and the depth of the recesses adjacent to the curved surface may be about 0.25 millimeters (mm).

With reference again to FIGS. 3-7, the porous layers 100 and 200 may be disposed in the reliefs 75 and 85 (FIGS. 8-11), respectively. For example, as shown in FIG. 4, the porous layers 100 and 200 may have a constant thickness so that when they are secured to and in the reliefs, outer portions 110 and 210 of porous layers 100 and 200 extend away from first surface 70 and second surface 80, respectively. As shown in FIG. 4, outer portions 110 and 210 act as a structure for providing a press fit or form teeth 115 and 215, respectively, to engage the sides of the bone cutout in the humeral head to better secure the implant apparatus 50 to the humeral head. The porous layers may have a constant thickness and are cut into a segment having an arc such as a section of the circumference of a circle, and a chord such as a straight line joining the two ends of the arc. See, FIGS. 3, 6 and 7. In other embodiments, the depth of the reliefs may be constant, and the porous member alone may be tapered.

Figure 7:
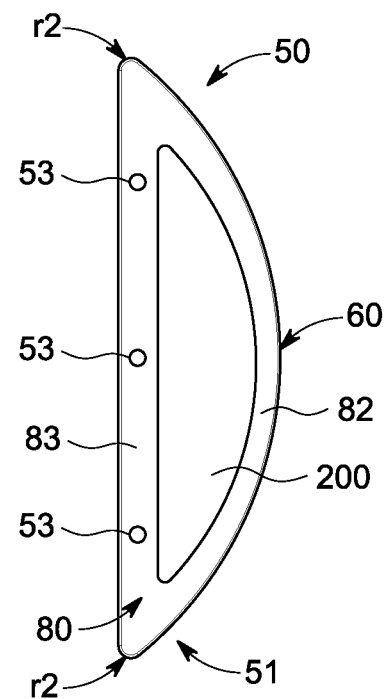
FIG. 7 is a second side view of the implant apparatus of FIG. 3, according to an embodiment of the present disclosure.
Figure 8:
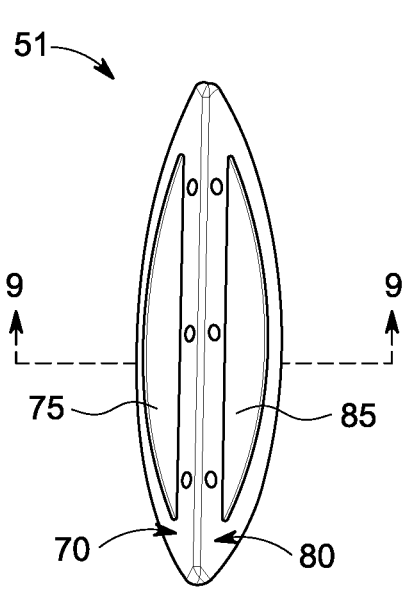
FIG. 8 is a bottom view of the implant body of the implant apparatus of FIG. 3, according to an embodiment of the present disclosure.

As shown in FIGS. 5-7, a plurality of through holes 53 may extend from first surface 70 to second surface 80. The through holes 53 may allow for supplemental fixation of the implant apparatus to the humeral head. For example, a suture (not shown) may be passed through one or more of the through holes and passed through a small tunnel in the humeral head to a suture button (not shown). The through holes may also allow for interdigitation with bone cement when the device is implanted with a cemented surgical technique.

Figure 12:
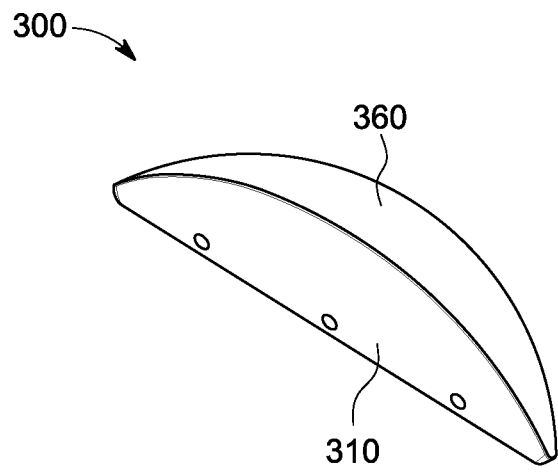
FIG. 12 is a perspective view of an implant, according to an embodiment of the present disclosure.

FIG. 12 illustrates an implant 300 according to an embodiment of the present disclosure. In this illustrated embodiment, the implant 300 may be a one-piece, integral, or monolithic structure formed from a single material. The implant 300 may have a curved surface 360, a first flat surface 310, and a second flat surface (not shown in FIG. 12).

Figure 13:
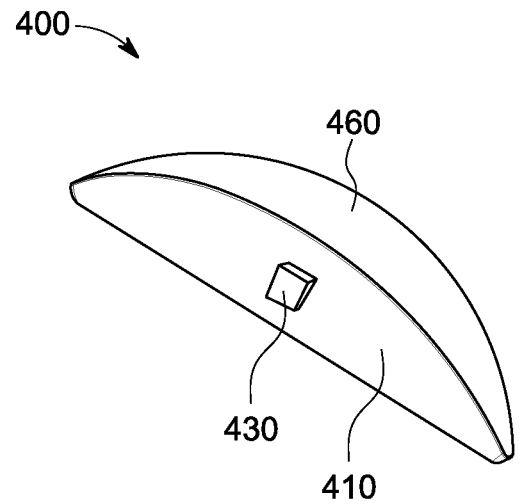
FIG. 13 is a perspective view of an implant, according to an embodiment of the present disclosure.

FIG. 13 illustrates an implant 400 according to an embodiment of the present disclosure. In this illustrated embodiment, the implant 400 may be a one-piece, integral, or monolithic structure formed from a single material. The implant 400 may have a curved surface 460, a first surface 410, and a second surface (not shown in FIG. 13). The first surface 410 may include a detent, tooth, barb, or other projection 430 that may be tapered or not tapered. A second surface (not shown in FIG. 13) may include a detent, tooth, barb, or other projection that may be tapered or not tapered that extends from the remainder of the second surface. The projections aid in forming a press fit or engageable portion to securely retain the implant in a cutout made in the humeral head. In other embodiments, more than one projection may be disposed on each side 410 of the implant.

Figure 14:
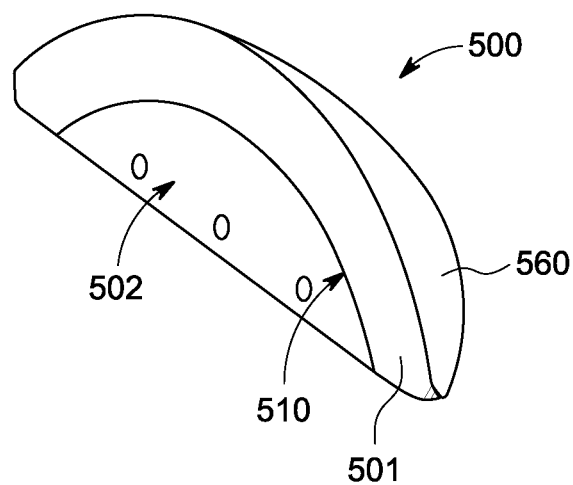
FIG. 14 is a perspective view of an implant apparatus, according to an embodiment of the present disclosure.

FIG. 14 illustrates an implant 500 according to an embodiment of the present disclosure. In this illustrated embodiment, the implant 500 may be a two piece structure. The implant 500 may have an upper portion 501 and a lower portion 502. The upper portion 501 may include a curved surface 560. Portions of the upper portion 501 and the lower portion 502 may form a first flat surface 510, and a second flat surface (not shown in FIG. 14).

In some embodiments, the humeral head implants and implant apparatus may be made out of a standard metallic implant material, such as titanium, cobalt chrome, or other acceptable stainless steels. In other embodiments, the humeral head implants and implant apparatus could be made of a polymeric material such as UHMWPE, polyurethane, PEEK, or a hydrogel. Further examples of suitable polymeric materials are described in U.S. Pat. No. 7,662,954, issued to James, et al., entitled "Outer Layer Having Entanglement Of Hydrophobic Polymer Host And Hydrophilic Polymer Guest", which is incorporated herein by reference in its entirety. The curved surface of the implant and implant apparatus can be machined to create a contour that closely matches the curvature and shape of the normal articulating surface of the humeral head. In other embodiments, the implant or body of the implant may be molded to shape. The implant body may be solid and not hollow, or may include one or more hollow portions or cavities.

The sides of the implants or implant apparatus that interact with the bone can have a surface treatment such as porous coating, HA coating, titanium plasma spray, or grit blasting, which will allow for a higher coefficient of friction to better fix the implant in the cutout of the humeral head and promote bone in growth. The implants and implant apparatus may be affixed to the humeral head with a pin, stem, screw, or combination thereof in order to prevent movement, prevent the implant from sliding out of the prepared cutout site in the humeral head, and facilitate bone in growth.

The porous layer, such as porous layers 100 and 200 (FIGS. 3-6) may be formed from a sheet material and cut to shape. The porous layer may be formed from titanium or tantalum-based structures, or other suitable material or materials. In other embodiments, the porous layer may be a sprayed or sintered on porous coating.

The implants and implant apparatus may be designed in multiple sizes to allow selection by a surgeon based on the width and depth of the particular lesion being treated. For example, as shown in FIG. 15, a plurality of differently sized and shaped implant and implant apparatus based on the normal surface anatomy of the humeral head may be provided, which correspond to Table 1 below.

TABLE 1

| | Radius | Depth first side | Depth second side | Angle |
|---|---|---|---|---|
| a) | 20 mm | 12 mm | 12 mm | 55° |
| b) | 20 mm | 10 mm | 10 mm | 55° |
| c) | 20 mm | 8 mm | 8 mm | 60° |
| d) | 23 mm | 12 mm | 12 mm | 55° |
| e) | 23 mm | 10 mm | 10 mm | 55° |
| f) | 23 mm | 8 mm | 8 mm | 60° |
| g) | 26 mm | 12 mm | 12 mm | 55° |
| h) | 26 mm | 10 mm | 10 mm | 55° |
| i) | 26 mm | 8 mm | 8 mm | 60° |
| j) | 28 mm | 12 mm | 12 mm | 55° |
| k) | 28 mm | 10 mm | 10 mm | 55° |
| l) | 28 mm | 8 mm | 8 mm | 60° |

Figure 15:
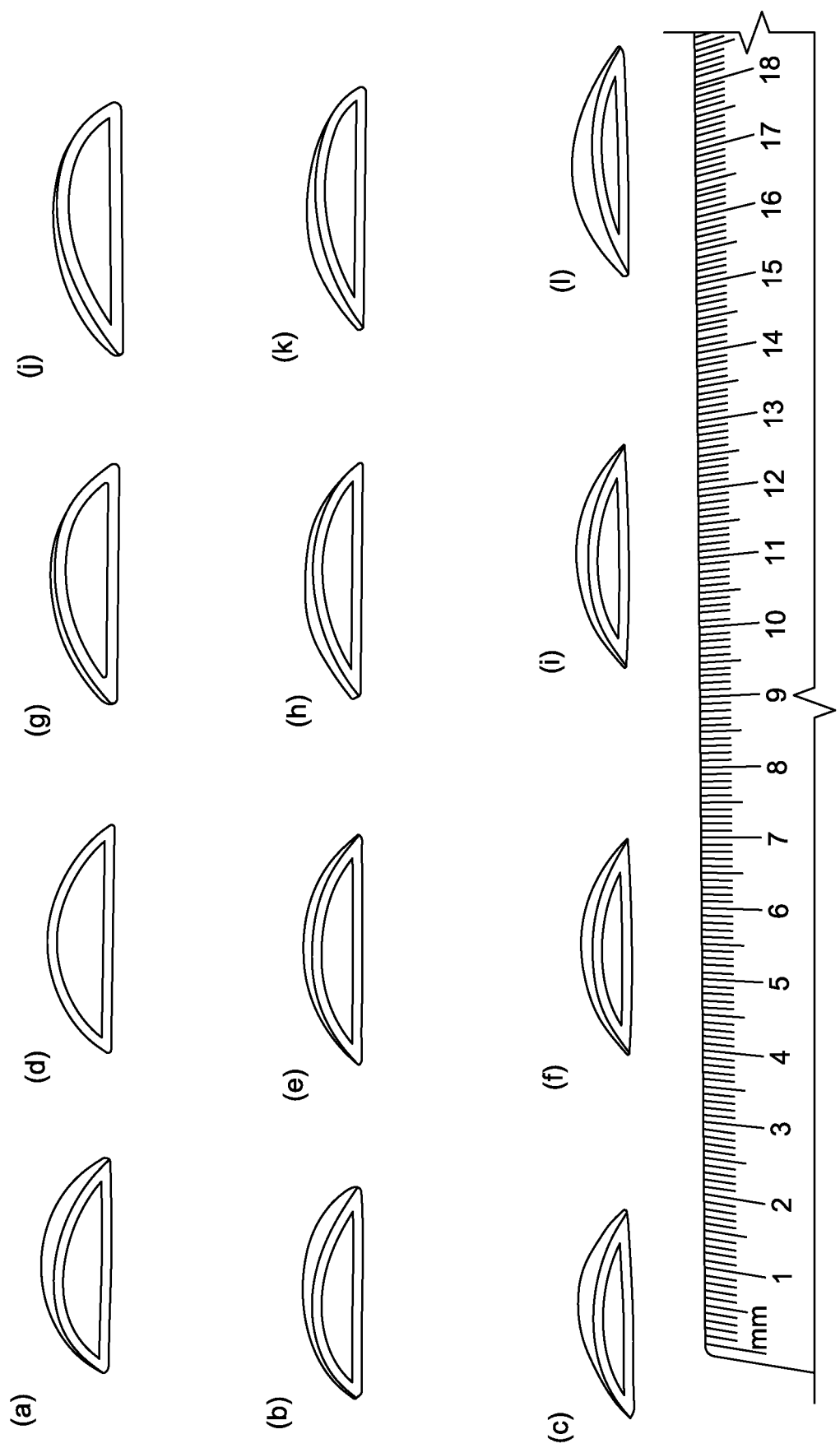
FIG. 15 illustrates representative side views of implants and/or implants apparatus, according to embodiments of the present disclosure.

As is noticed in FIG. 15, in moving from the left column to right column the radius of curvature increases but with angle between the two sides of the implant remaining the same. In moving from the bottom row to the top row the depth and angle of the implant increases, e.g., resulting in a greater volume of the implant. While 12 different implants sizes and configurations are illustrated, it will be appreciated that fewer or more differently sized and configured implants may be acceptable in covering the typical range of different sized and shaped anatomic humeral heads.

With reference to FIGS. 16-18, therein illustrated is a cutting guide system 600 according to an embodiment of the present disclosure for facilitating the precise preparation of, for example, a humeral head to receive the preconfigured, pre-sized implant or implant apparatus. The cutting guide system is designed to work in either a deltopectoral or a posterior approach (open incision). As described below, different sized cutting guide system may be provided, which fit the size and configuration of the humeral head and the lesion to form a specifically sized cutout that corresponds to the size and configuration of the implant or implant apparatus to be installed in the cutout in the humeral head.

In this illustrated embodiment, the cutting guide system 600 includes a body 610 and a plurality of pins 650 for securing the cutting guide system 600 to the humeral head during the cutting of the humeral head around a lesion 15 (FIG. 16). The body 610 includes an inner contoured surface 620 (best shown in FIG. 17) and an outer surface 630. The cutting guide system 600 includes a window or opening 615 (FIGS. 16 and 18) defining a first cutting guide surface 660 (FIG. 18) that extends from outer surface 630 to inner surface 620 (FIG. 18), and a second cutting guide surface 670 (FIG. 18) that extends from outer surface 630 to inner surface 620 (FIG. 18). The first cutting guide surface 660 (FIG. 18) is disposed at an angle C (FIG. 18) relative to the second cutting guide surface 670 (FIG. 18). A plurality of through holes 680 may extend through the body 610 and be disposed adjacent to the first cutting surface 670 (FIG. 18) for receiving the pins 650. The plurality of through holes 680 may be placed in a location to span over the greater tuberosity as well as the inferior neck of the humerus. Body 610 may be a one-piece, integral, or monolithic structure formed from a single material. The body may be formed from plastic or stainless steel. In other embodiments, the body may include multiple components. The pins may be Steinmann pins having a screw, chisel or trocar end for engaging the humeral head.

The cutting guide system is designed to fit onto the posterior half of the humeral head. The cutting guide system can be positioned over the lesion, then secured to the humerus using the pins. The cutting guide system allows the surgeon to resect the bone immediately around the lesion using either a chisel or an oscillating saw blade. The cutting guide system controls the depth and the width of the cut to ensure the correct fit of a corresponding selected implant or implant apparatus. The cutting guide system may include slotted features to control the path of the chisel or blade.

With reference again to FIGS. 2 and 4, for example, the angle A (FIG. 2) of the cutout 20 (FIG. 2) may be the same angle A (FIG. 4) of the body 51 (FIG. 4) of the implant apparatus 50 (FIG. 4). Outer surfaces of porous layers 100 and 200 (FIG. 4), respectively, may define an angle B (FIG. 4) that is greater than angle A (FIG. 2) resulting in a press fit or interference fit of the flared out portions of the porous layers 100 and 200 (FIG. 4) when the implant apparatus 50 (FIG. 4) is placed in the cutout 20 (FIG. 2) of the humeral head 12 (FIG. 2), and pushed downwardly to seat the entirety of the implant apparatus 50 (FIG. 4) in the cutout 20 (FIG. 2) in the humeral head 12 (FIG. 2). Portions of the edges of the porous material prevent movement of the implant apparatus out of the cutout. For example, the upper curved portions of the porous material aid in preventing upward superior movement of the implant apparatus out of the cutout, and portions of the lower lateral edges of the porous material aid in preventing longitudinal (lateral/medial) movement of the implant apparatus relative to the cutout in the humeral head.

FIGS. 19-26 illustrate a drill guide 700 (FIG. 19) and a cutting guide system 750 (FIGS. 22 and 23) for forming, for example, a cutout in a humeral head, which cutout is sized for receiving a corresponding implant or implant apparatus.

Figure 19:
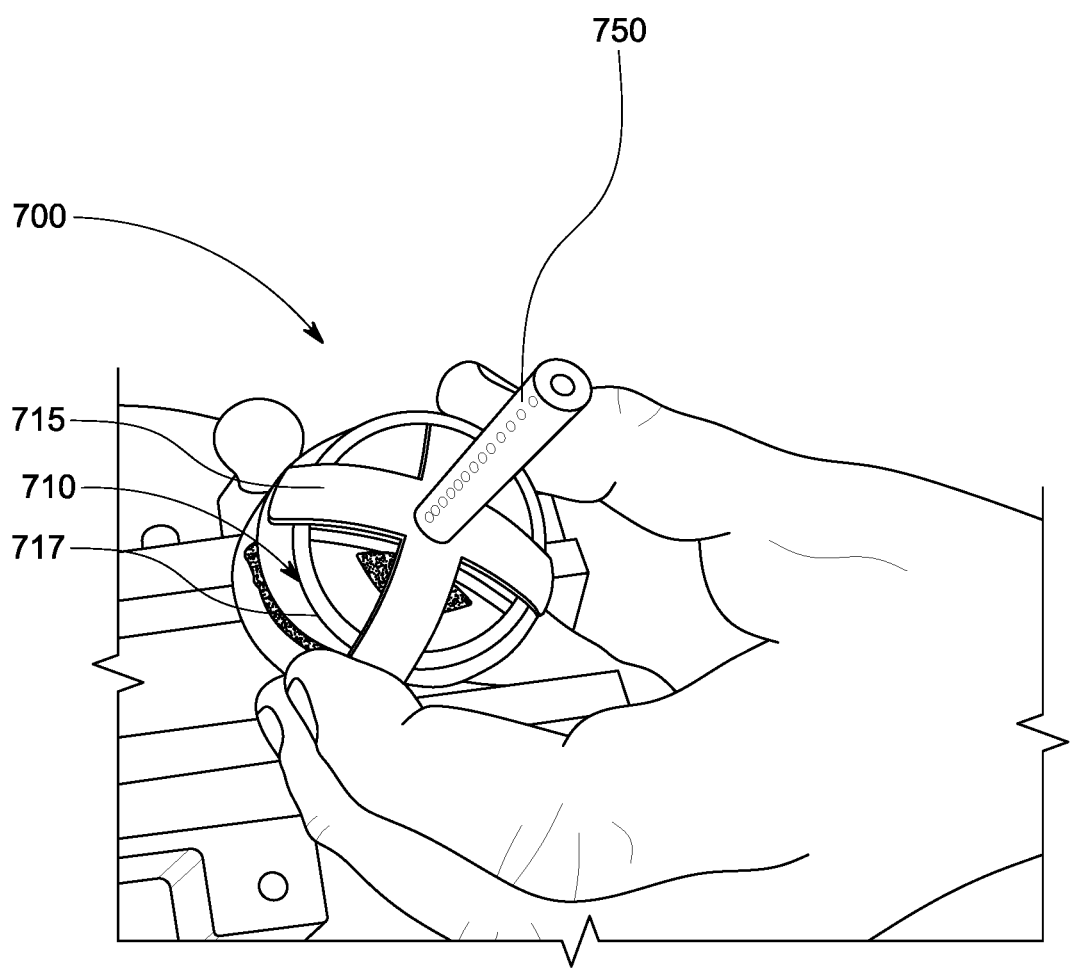
FIG. 19 is a perspective view of a drill guide positioned on the humeral head, according to an embodiment of the present disclosure.
Figure 20:
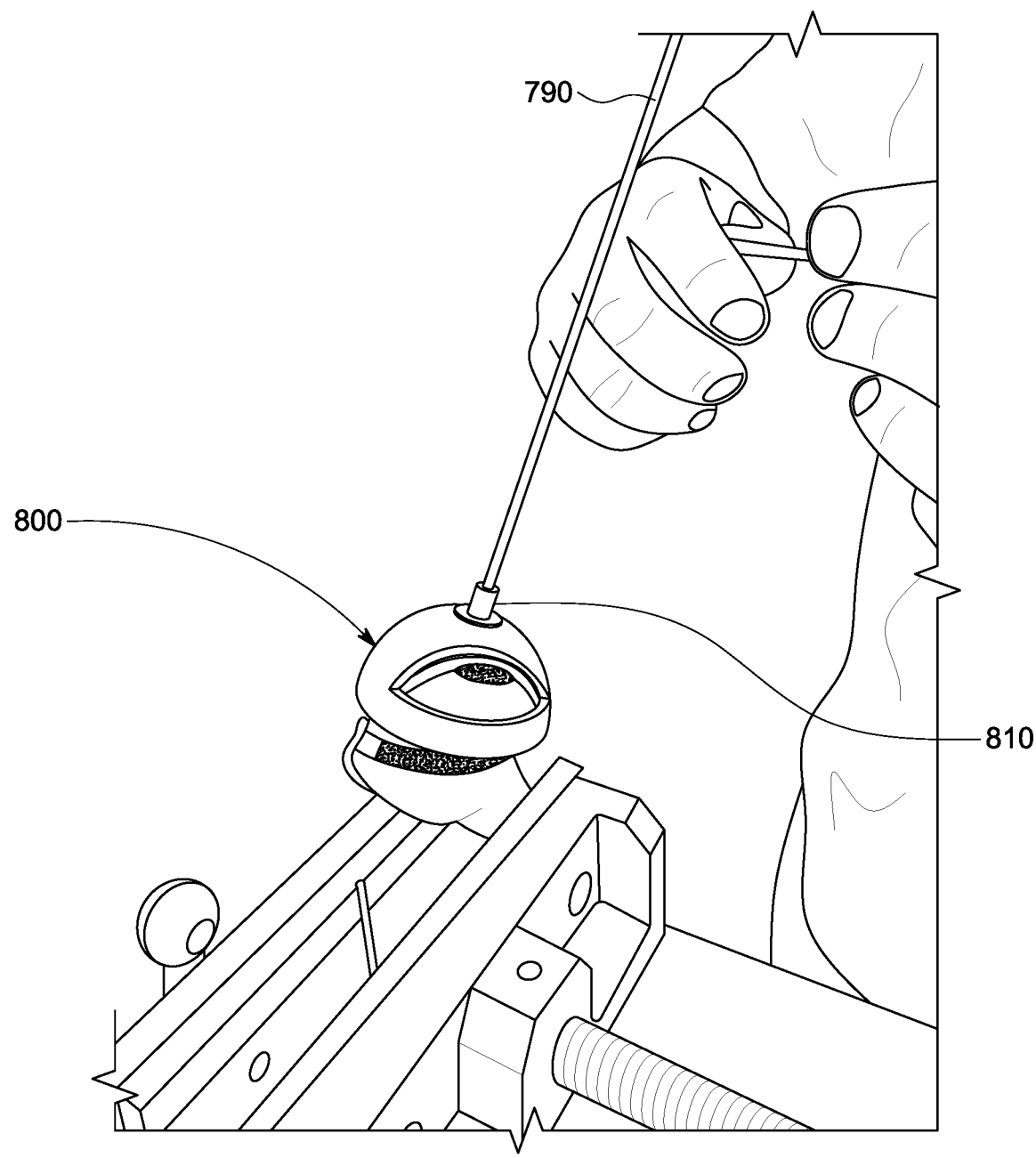
FIG. 20 is a perspective view of a cutting support of a cutting guide system attached to the humeral head of FIG. 19, according to an embodiment of the present disclosure.

In this illustrated embodiment, as shown in FIG. 19, the drill guide 700 includes a sizing support 710 and a pilot nail guide 750 to size the humeral head and guide the placement of a pilot nail 790 (FIG. 20). The sizing support 710 may include a plurality of curved arms 715 and ring 717 that defines an inner curved surface. In some embodiments, a plurality of differently sized drill guides may be provided for a surgeon. For example, four (4) different drill guides, each having a different inner curved surface may be provided to cover the typical range of the different sizes of patients' humeral heads. Once a surgeon determines the correct drill guide, the surgeon can position the drill guide relative to the lesion observable between the curved arms 715 for positioning the pilot nail guide 750. The pilot nail may be guided by the pilot nail guide 750 into the humerus, and then, the drill guide 700 may be slid off the pilot nail.

Figure 21:
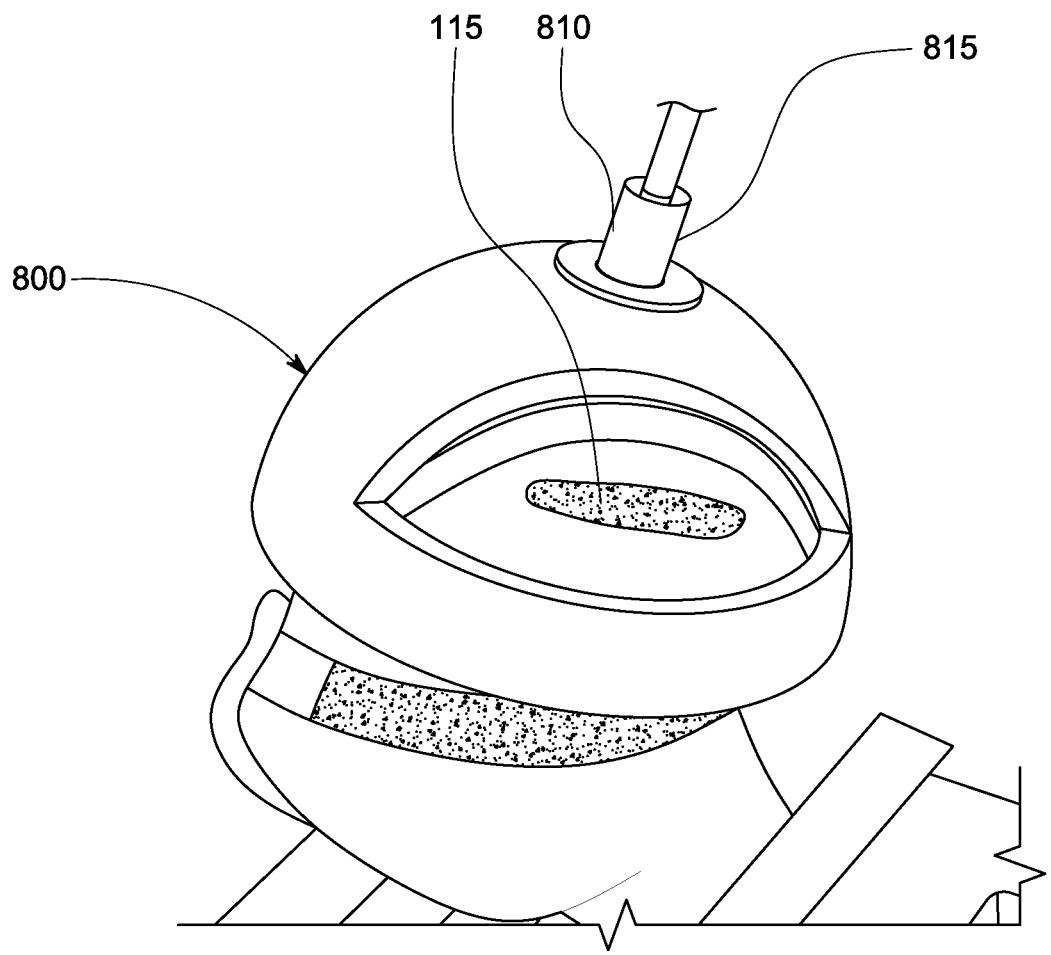
FIG. 21 is an enlarged perspective view of the cutting support of FIG. 20, according to an embodiment of the present disclosure.

FIG. 20 illustrates a humeral cut guide support 800 having a corresponding inner curved surface to the drill guide 700 (FIG. 19) and a projection or tab 810 having a passageway. The passageway of projection 810 of the support 800 may slide over the pilot nail 790. Projection 810 may include an indexing tab 815 extending from the projection 810 as shown in FIG. 21.

Figure 22:
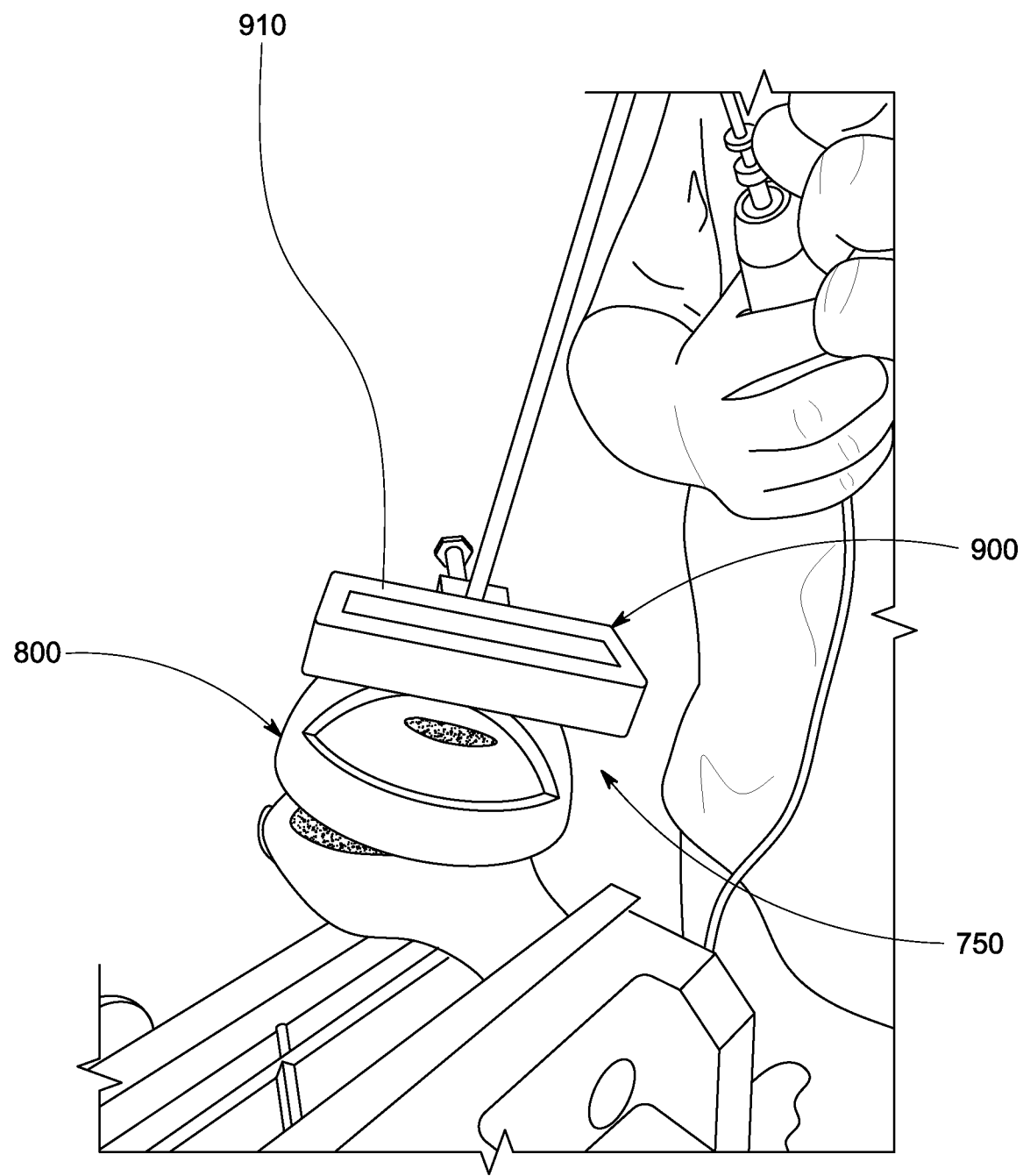
FIG. 22 is a perspective view of a milling guide attached to the cutting support of FIG. 20 to form the cutting guide system, according to an embodiment of the present disclosure.

With reference to FIG. 22, a milling guide 900 includes an elongated groove 910 that is operably fixedly attachable to the cut guide support 800. For example, the milling guide 900 may include a corresponding sized cavity (not shown), which fits on the projection 810 (FIG. 21) and indexing tab 815 (FIG. 21). An adjustable thumb screw (not shown in FIG. 22) allows the surgeon to secure the milling guide to the cut guide support.

Figure 23:
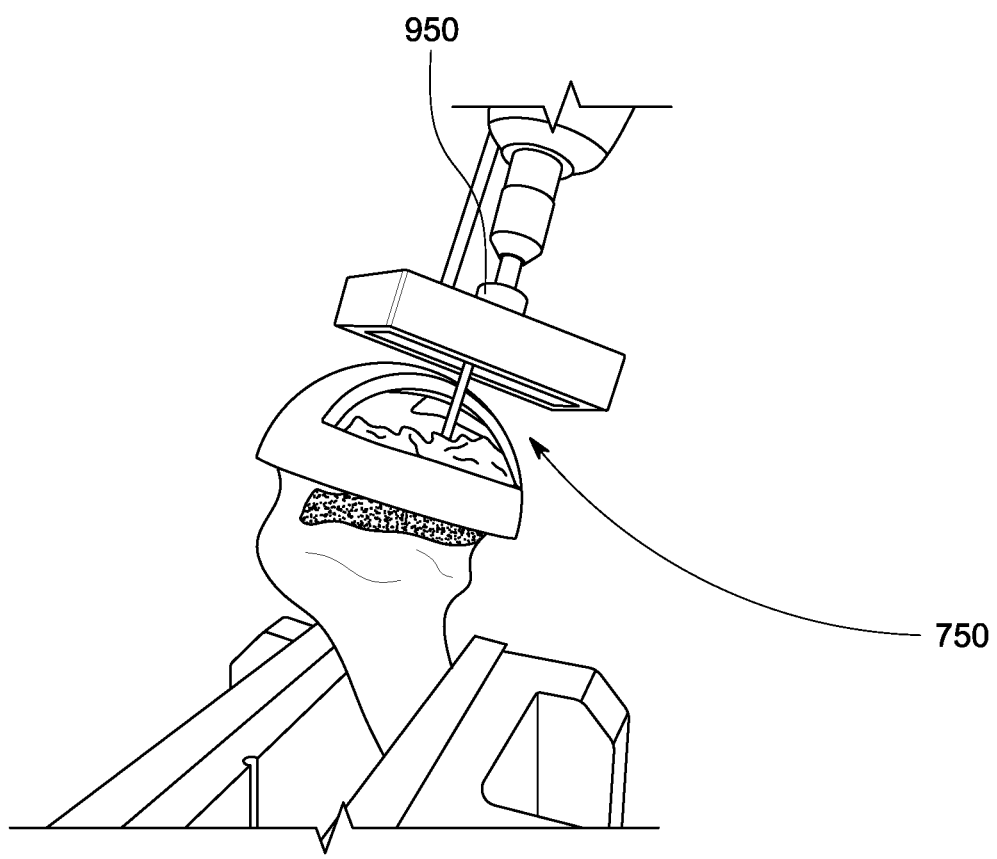
FIG. 23 is a perspective view of a milling bit disposed in the milling guide of FIG. 22 during milling of the humeral head, according to an embodiment of the present disclosure.
Figure 24:
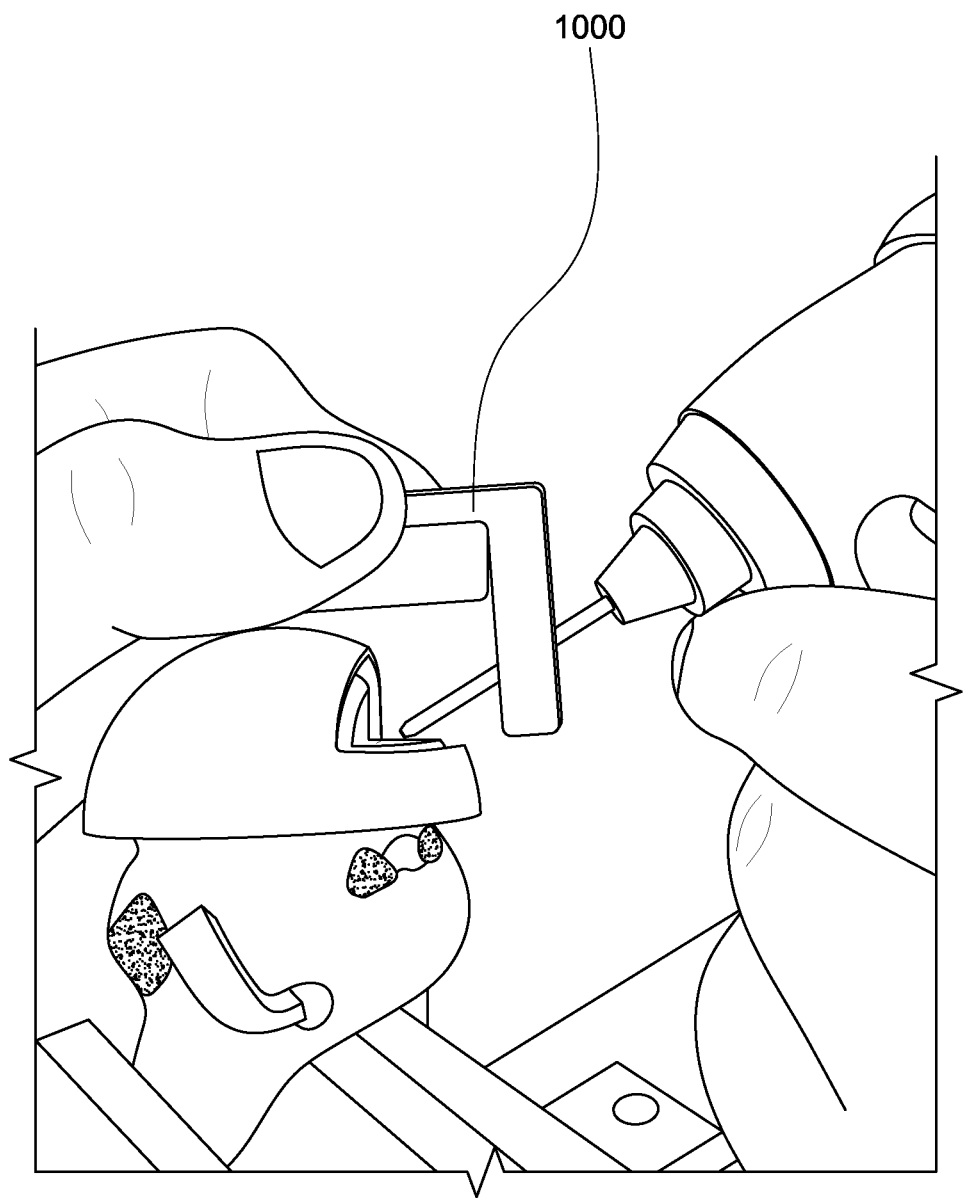
FIG. 24 is a perspective view of a pilot guide hole guide operably attached to the cutting support of FIG. 20 during the milling of a pilot hole in the humeral head, according to an embodiment of the present disclosure.
Figure 25:
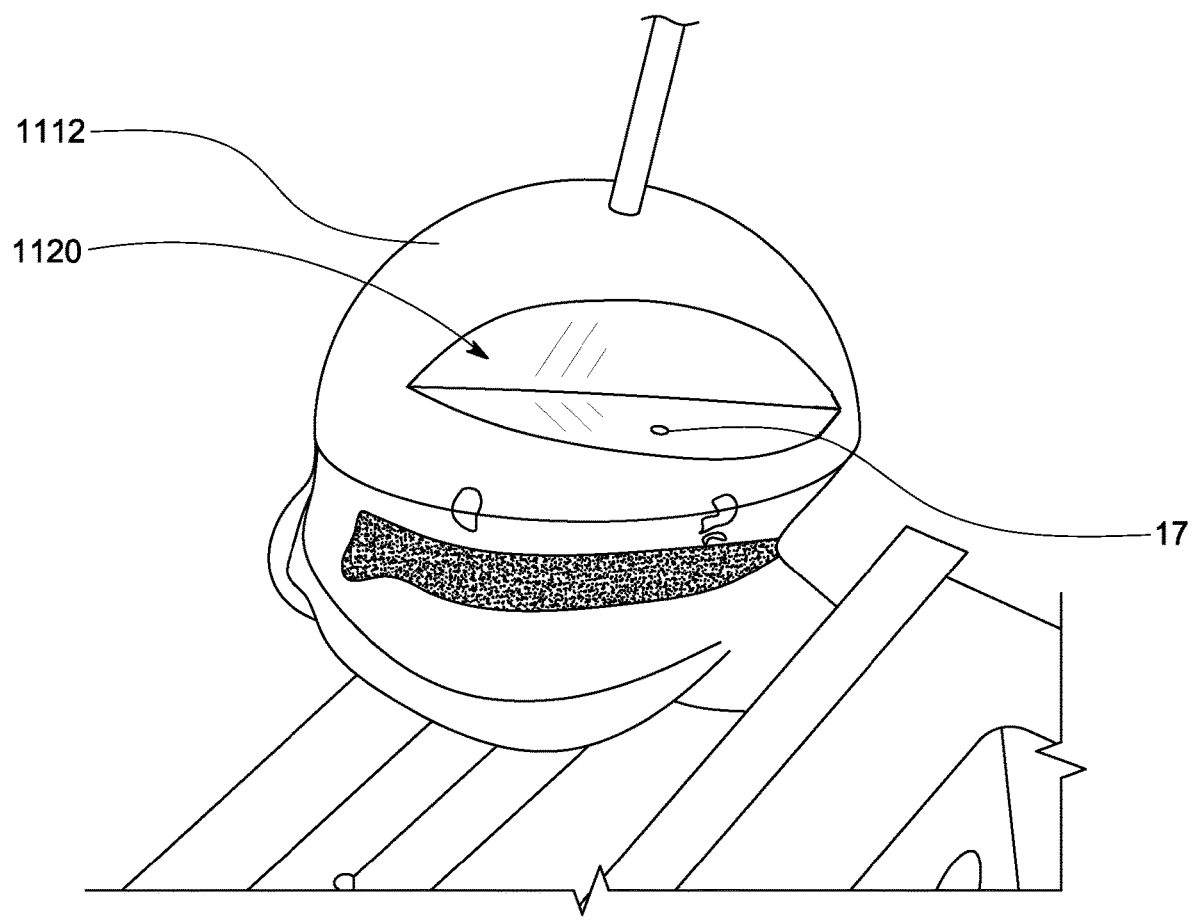
FIG. 25 is a perspective view of the humeral head of FIG. 24 having a cutout and a hole, according to an embodiment of the present disclosure.

As shown in FIG. 23, a surgeon can use a mill cutting tool having a stop collar 950 to traverse the elongated groove 910 (FIG. 22) and form the cutout in the humerus. The elongated groove 910 (FIG. 22) in the milling guide has a width that allows the surgeon to move the milling tool across the elongated groove 910 (FIG. 22) to cut the width of the lower side of the cutout. FIG. 24 illustrates a drill guide 1000 having a tongue (not shown in FIG. 24) extending along the length and receivable in the groove 910 (FIG. 22) of the milling guide 900 (FIG. 22), in which the drill guide 1000 is operable to guide a drill at a specific angle to form a hole 17 into humeral head 1112 as shown in FIG. 25. The hole 17 has an opening onto a surface of the cutout 1120 in the humeral head 1112.

As shown in FIG. 26, an implant or implant apparatus 1050 includes a post 1051, shown in FIG. 27, extending from the implant or implant apparatus 1050, which post 1051 is receivable in the cutout 1120 (FIG. 25) in the humeral head 1112 (FIG. 25) and operable to hold the implant or implant apparatus 1050 in place. The post 1051 of the implant or implant apparatus may be press fit into the hole 17 (FIG. 25) to provide addition support to maintain the position of the implant or keep the implant apparatus from sliding along the length of the cutout. In other embodiments, two or more posts may be provided. The post 1051 can have a surface treatment such as porous coating, HA coating, titanium plasma spray, or grit blasting, which will allow for a higher coefficient of friction to better fix the implant in the cutout of the humeral head and promote bone in growth.

FIG. 28 illustrates an implant 2050 according to an embodiment of the present disclosure. In this illustrated embodiment, the implant 2050 may be a one-piece, integral, or monolithic structure formed from a single material, or may be formed from two or more different pieces or materials. The implant 2050 may have a curved surface 2360, a first flat surface (not shown in FIG. 28), and a second flat surface (not shown in FIG. 28). Implant 2050 may include through holes 2055 in the implant that extend through the curved surface 2360. The holes 2055 are operable to accept screws (not shown in FIG. 28) that would pass through the implant to secure the implant to the bone.

In some embodiments, for each cut guide or cutting guide system there would be a corresponding implant or implant apparatus. The cutting guide system of the present disclosure may be reusable tools or single use tools. In other embodiments, a cut guide or cutting guide system may be operably adjustable, e.g., the angle and/or the depth of the cut to be made, so as to be used with any number of implants or implant apparatus that may be selected to be received in a cutout. The implants and implant apparatus may be sterile and packaged individually. A surgeon can start with a first selected cutting guide system, and if it is not adequate to remove the lesion, the surgeon can then use another cutting guide system to enlarge the cutout that provides for a larger sized implant or implant apparatus. Only after finalizing the size of the cutout, a surgeon can then open a sterile packaged of the corresponding implant or implant apparatus.

FIG. 29 illustrates a "radius guide" or tool 3000, according to an embodiment of the present disclosure, which can be used by a surgeon to measure the curvature, for example, of the humeral head surface such as outside of the lesion area. The tool 3000 can be used at the start of the surgery to confirm the radius of the humeral head of a particular patient, and thus, select the corresponding cutting guide and implant or implant system. The tool 3000 may include a generally planar structure 3100 having a plurality of different curved edges, for example, curved edge 3210 having a radius Z1, curved edge 3220 having a radius Z2, curved edge 3230 having a radius Z3, and curved edge 3240 having a radius Z4.

Figure 30:
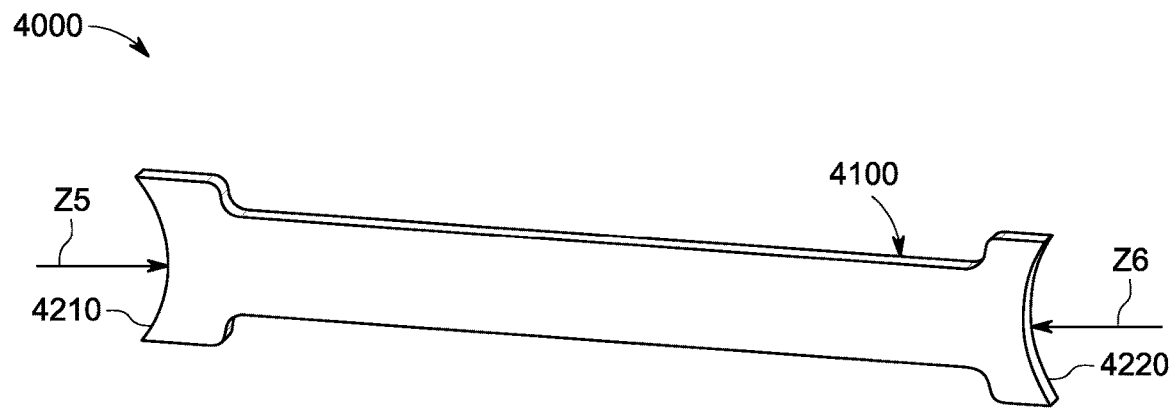
FIG. 30 is a perspective view of a tool for measuring the radius of a humeral head, according to an embodiment of the present disclosure.

FIG. 30 illustrates a "radius guide" or tool 4000 that can be used by a surgeon to measure the curvature of, for example, the humeral head surface such as outside of the lesion area. The tool 4000 can be used at the start of the surgery to confirm the radius of the humeral head of a particular patient, and thus, select the corresponding cutting guide and implant or implant system. The tool 4000 may include a generally elongated planar structure 4100 having a plurality of different curved edges, for example, at a first end a curved edge 4210 having a radius Z5, and at a second end a curved edge 4220 having a radius Z6. A plurality of tools 4000 may be provided to cover four or more different radius. The tool 4000 may allow the user to hold the tool 4000 further away from one's hand, and may be smaller compared to tool 3000 (FIG. 29) to allow tool 4000 to more easily fit an incision area to access the humeral head. A length of the tool 4000 from one end to the other may be about 6 inches and the width of the ends may be about 1 inch. The radius of the ends may be marked, stamped, printed or otherwise noted adjacent to the ends. The tool may be made out of stainless steel or engineering plastic so that it may be reusable.

Figure 31:
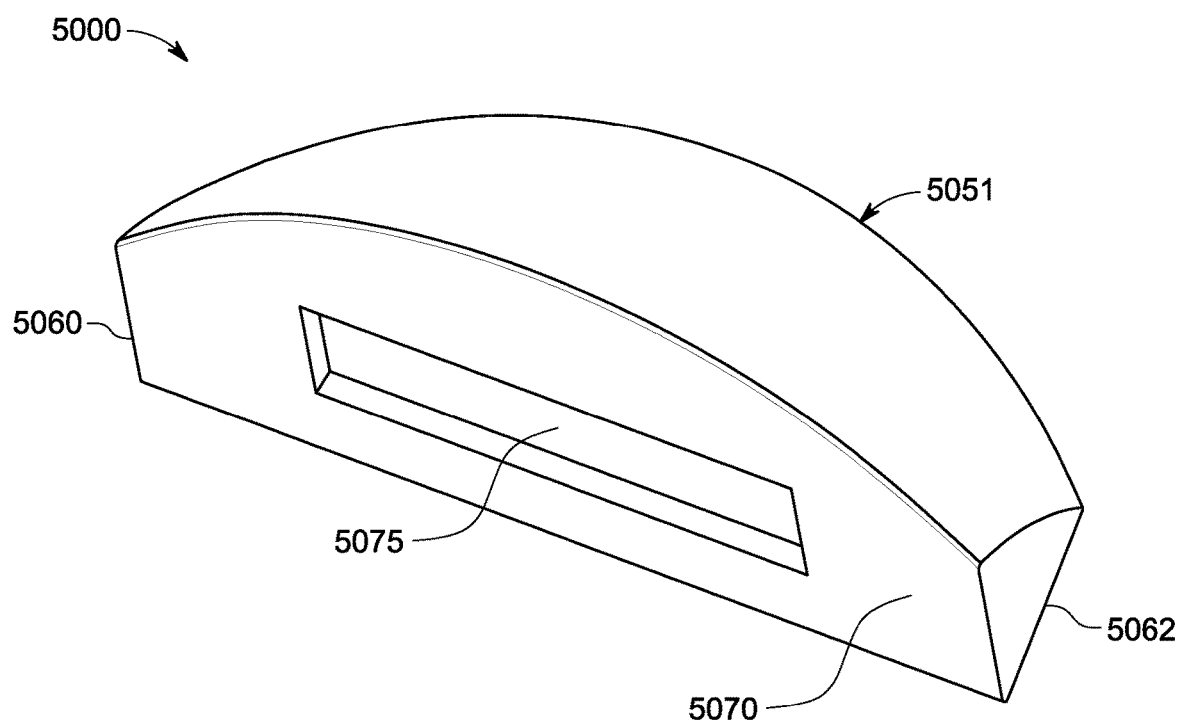
FIG. 31 is a perspective view of an implant body, according to an embodiment of the present disclosure.

FIG. 31 illustrates an implant apparatus 5000 having a body 5051 (the porous layers not shown), according to an embodiment of the present disclosure, of an implant apparatus without the porous later (not shown). The body 5051 may be essentially the same as body 50 (FIGS. 8-11) with the same wedge geometry but with the exception of shortened or truncated ends of the body. For example, a first surface 5070 of body 5051 may include a first recess or relief 5075 disposed generally in the center of first surface 5070. A second surface (not shown) of body 5051 may include a second recess or relief (not shown) disposed generally in the center of the second surface. The first surface 5070 may define a first flat surface disposed around relief 5075. The second surface may define a second flat surface disposed around second relief. The reliefs may be tapered reliefs that extend into the first surface and the second surface similar to the reliefs 75 and 85 of body 51 (FIGS. 8-11).

In this illustrated embodiment, body 5055 may include shortened or truncated ends 5090 and 5092. Shortened or truncated ends may allow the implant apparatus to fit into a corresponding cutout in the humeral head to provide a buttress to prevent movement, sliding, or translation along the length of the implant apparatus relative to the corresponding cutout in the humerus head.

Figure 32:
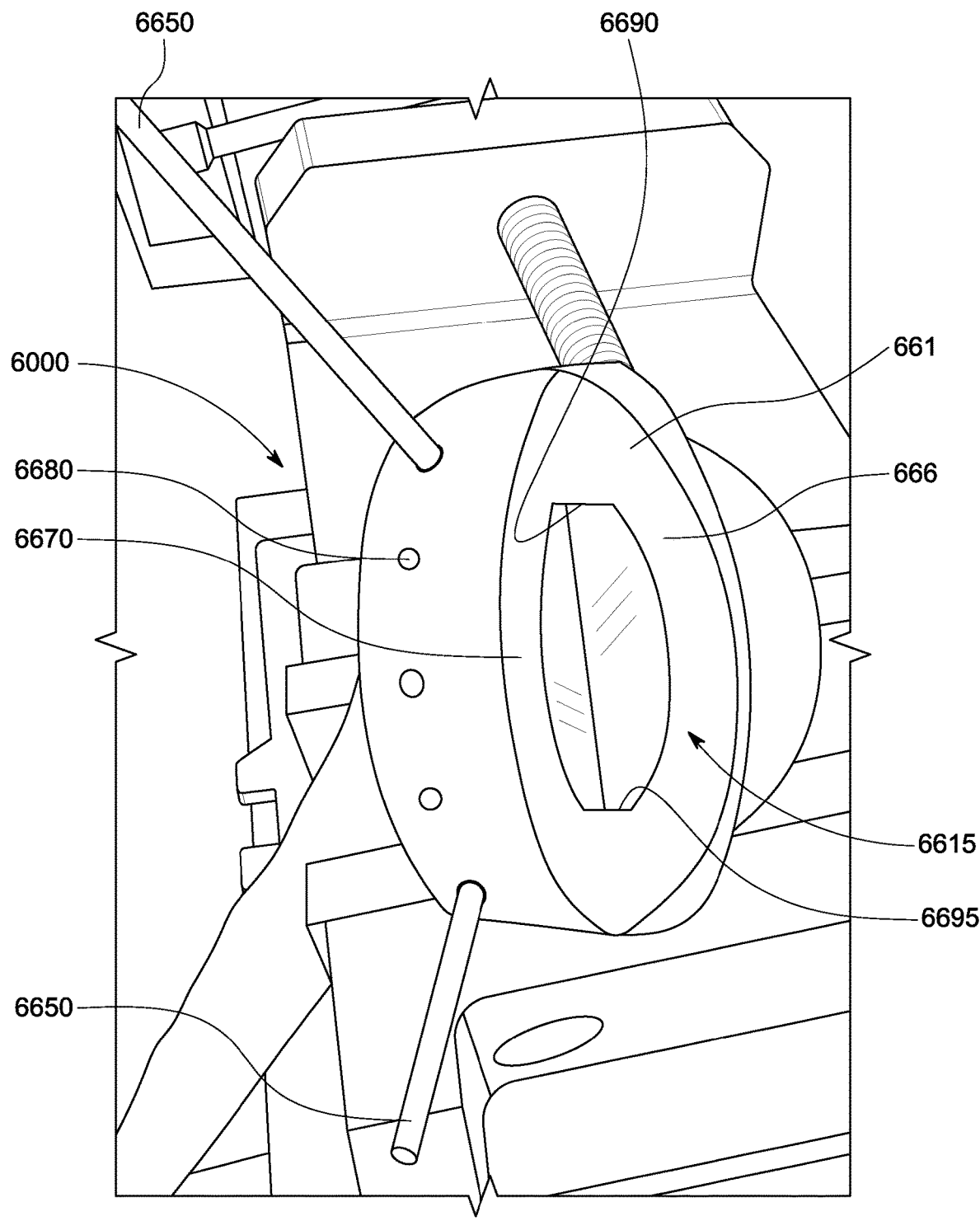
FIG. 32 is a perspective view of a cutting guide system secured to the humeral head after forming a cutout in the humeral head for receiving a humeral implant apparatus having the implant body of FIG. 31, according to an embodiment of the present disclosure.

With reference to FIG. 32, therein illustrated is a cutting guide system 6600 for facilitating preparation of the humeral head to receive the preconfigured, pre-sized implant or implant apparatus such as the implant apparatus having body 5051 (FIG. 31). The cutting guide system is designed to work in either a deltopectoral or a posterior approach (open incision). As described, different sized cutting guide system may be provided, which fit the size and configuration of the humeral head and the lesion to form a specifically sized cutout that corresponds to the size and configuration of the implant or implant apparatus to be installed in the cutout in the humeral head.

In this illustrated embodiment, the cutting guide system 6000 includes a body 6610 and a plurality of pins 6650 for securing the cutting guide system 6000 to a humeral head during the cutting of the humeral head around a lesion. The body 6610 includes an inner contoured surface and an outer surface. The cutting guide system 6600 includes a window or opening 6615 defining four cutting surfaces. For example, cutting guide system 6600 may include a first cutting guide surface 6660 that extends from the outer surface to the inner surface, a second cutting guide surface 6670 that extends from the outer surface to the inner surface, a third cutting guide surface 6690 that extends from the outer surface to the inner surface, and a fourth cutting guide surface 6695 that extends from the outer surface to the inner surface.

The first cutting guide surface 6660 is disposed at an angle relative to the second cutting guide surface 6670. The third cutting guide surface 6690 and fourth cutting guide surface 6695 may be disposed parallel to each other and normal to the first and second cutting guide surfaces. A plurality of through holes 6680 may extend through the body 6610 and be disposed adjacent to the first cutting surface for receiving the pins 6650. The plurality of through holes 6680 may be placed in a location to span over the greater tuberosity as well as the inferior neck of the humerus. Body 6610 may be a one-piece, integral, or monolithic structure formed from a single material. The body may be formed from engineering plastic or stainless steel. In other embodiments, the body may include multiple components. The pins may be Steinmann pins having a screw, chisel or trocar end for engaging the humeral head.

Figure 33:
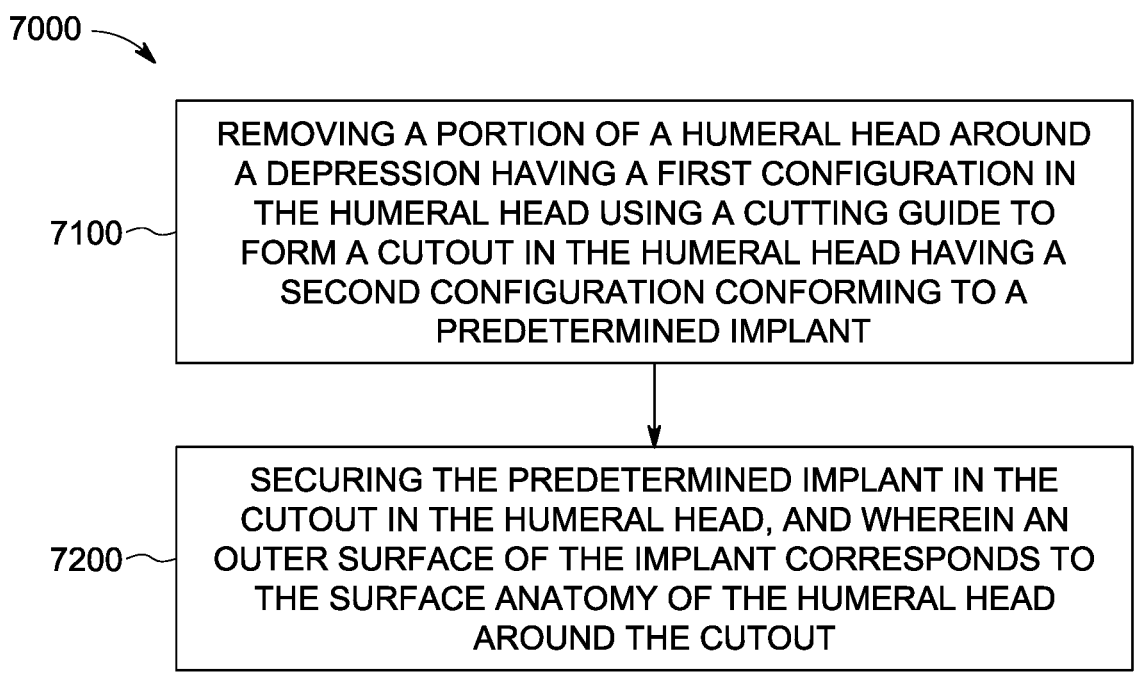
FIG. 33 is a flowchart of a process for repairing a humeral head, according to an embodiment of the present disclosure.

The cutting guide system is designed to fit onto the posterior half of the humeral head. The cutting apparatus can be positioned over the lesion, then secured to the humerus using the pins. The cutting guide system allows the surgeon to resect the bone immediately around the lesion using either a chisel, milling guide, saw blade, or other suitable cutting tool or combination thereof. The cutting guide system may control the depth and the width of the cut to ensure the correct fit of a corresponding selected implant or implant apparatus, for example, as described below FIG. 33 illustrates a method 7000 for repairing a humeral head. Method 7000 includes, for example, at 7100 removing a portion of a humeral head around a depression having a first configuration in the humeral head using a cutting guide to form a cutout in the humeral head having a second configuration conforming to a predetermined implant, and at 7200 securing the predetermined implant in the cutout in the humeral head, and wherein an outer surface of the implant corresponds to the normal surface anatomy of the humeral head around the cutout. The method may utilize the implants, implant apparatus, cutting guides, and cutting guide apparatus disclosed herein.

FIG. 34 illustrates a cutting guide system 8000, according to an embodiment of the present disclosure for facilitating preparation of, for example, a humeral head to receive a preconfigured, pre-sized implant or implant apparatus. The cutting guide system 8000 may generally include a support portion 8100 and an insert portion 8300, which when assembled define a first cutting guide or slot 8500 and a second cutting guide or slot 8550. The cutting guide system is designed to work in either a deltopectoral or a posterior approach (open incision). As described below, a plurality of differently sized cutting guide systems may be provided, which fit the size and configuration of the humeral head and the lesion to form a specifically sized cutout that corresponds to the size and configuration of the implant or implant apparatus to be installed in the cutout in the humeral head.

In this illustrated embodiment, the cutting guide system 8000 may include the support portion 8100 having a frame 8120 and the insert portion 8300 having a body 8301, which when the cutting guide system 8000 is assembled, e.g., the insert portion 8300 is received and disposed in the support portion 8100, the cutting guide system 8000 defines the first cutting guide or slot 8500 and the second cutting guide or slot 8550.

Figure 35:
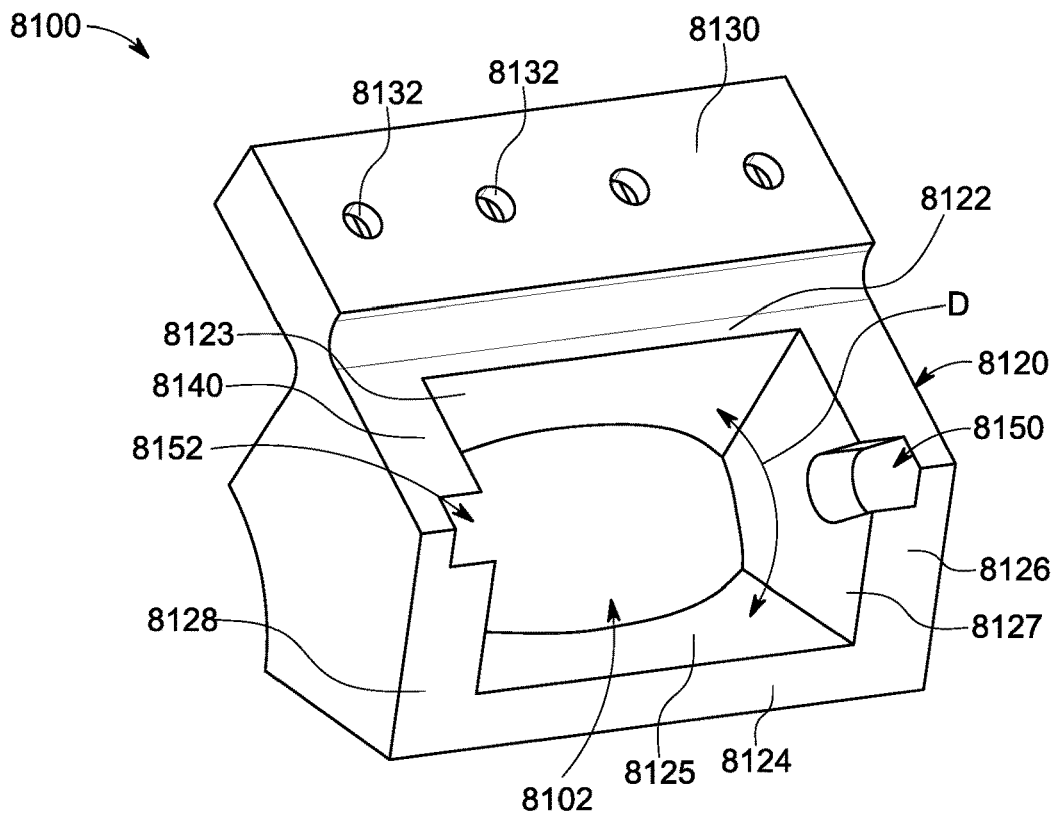
FIG. 35 is a top perspective view of the support portion of the cutting guide system of FIG. 34, according to an embodiment of the present disclosure.
Figure 36:
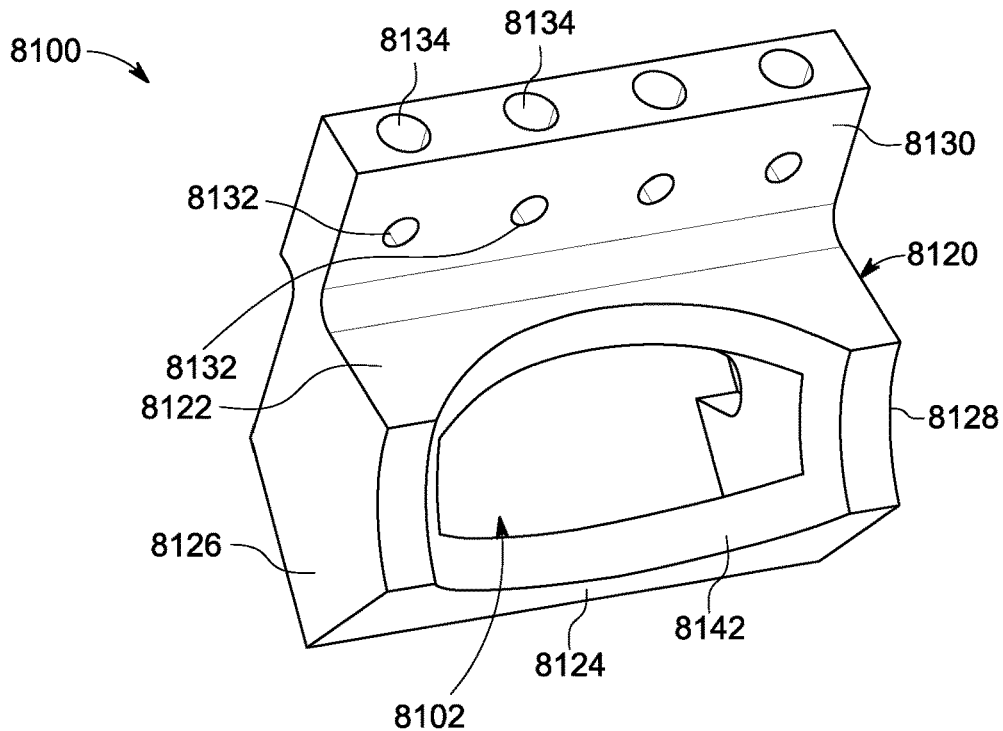
FIG. 36 is a bottom perspective view of the support portion of the cutting guide system of FIG. 35, according to an embodiment of the present disclosure.

With reference to FIGS. 35 and 36, the support portion 8100 may define the frame 8120 with an opening 8102 extending therethrough. For example, the frame 8120 may include a first side 8122, a second side 8124, a third side 8126, and a fourth side 8128. As shown in FIG. 35, the first side 8122 defines a first inside surface 8123, the second side 8124 defines a second inside surface 8125, the third side 8126 defines a third inside surface 8127, and the fourth side 8128 defines a fourth inside surface 8129. The third inside surface 8127 may be parallel to the fourth inside surface 8129. The third inside surface 8127 may include a first recessed elongated channel 8150, and the fourth inside surface 8129 may include a second recessed elongated channel 8152. The first inside surface 8123 is disposed at an angle relative to the second inside surface 8125. For example, the first inside surface 8123 of the frame 8120 and the second inside surface 8125 of the frame 8120 may be disposed at an angle D of between about 50 degrees and about 65 degrees. In some embodiments, the angle D may be between about 55 degrees and about 60 degrees, or other suitable angles. The opening 8102 defines a first guide and a second guide for resecting a cutout in a humeral head so that the cutout in the humeral head has a first surface and a second surface corresponding to a first surface and a second surface of a humeral implant. For example, the first inside surface 8123 of the frame 8120 may define a first guide, and the second inside surface 8125 of the frame 8120 may define the second guide.

With reference again to FIGS. 35 and 36, the frame 8120 may include a cantilevered portion 8130 extending from the first side 8122. A plurality of through-holes 8132 may extend through the cantilevered portion 8130 of the frame 8120 for receiving one or more pins 8101 (FIG. 37) for use in securing the support portion 8100 to a humeral head.

The frame 8120 defines an outer surface 8140 (FIG. 35) and an inner contoured surface 8142 (FIG. 36) in which inner contoured surface 8142 is disposable on a humeral head. For example, the contoured surface 8142 may be a concave surface. The concave surface 8412 may be offset from the cantilevered portion 8130.

Figure 37:
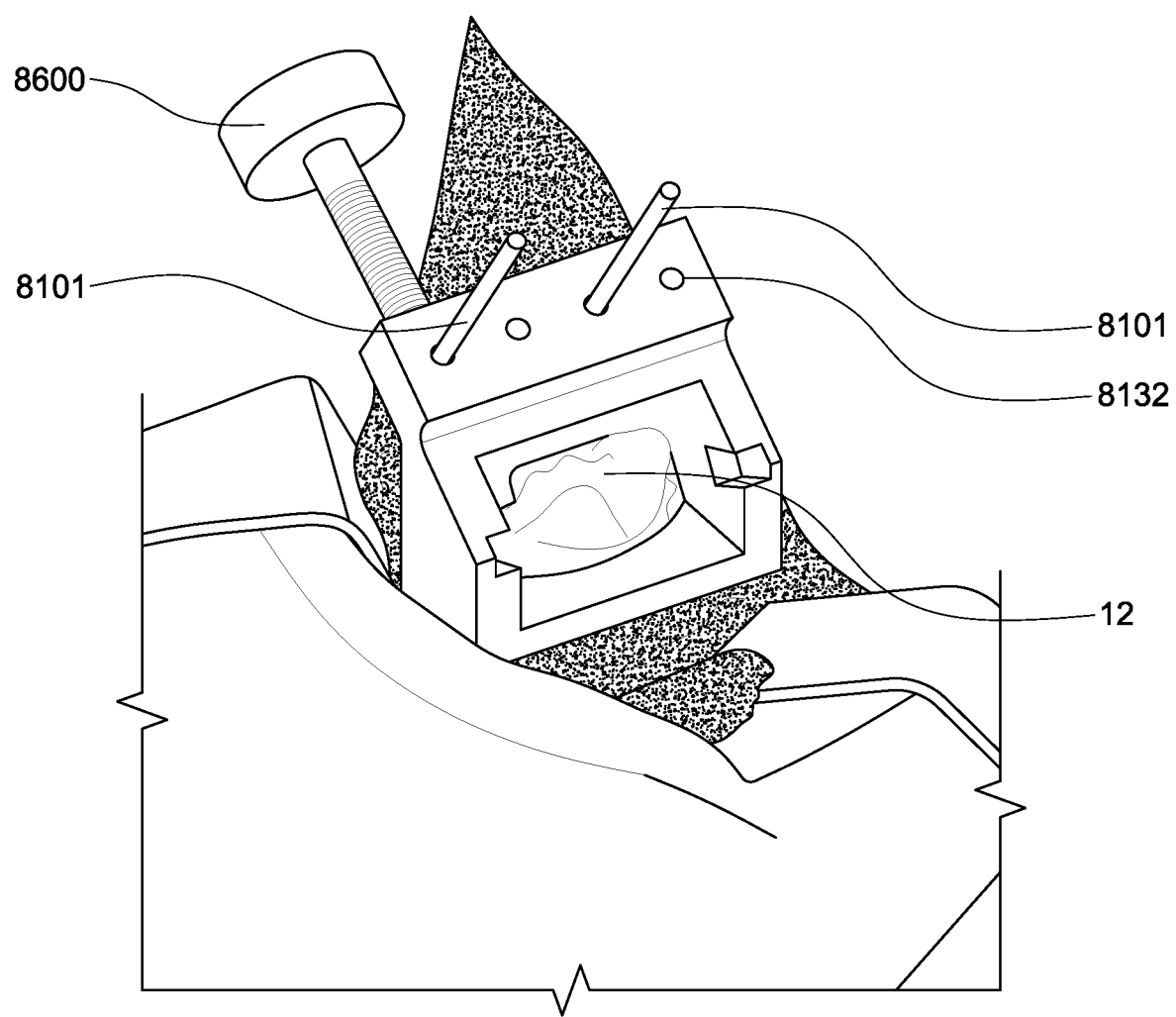
FIG. 37 is a perspective view of the support portion of the cutting guide system of FIG. 34 secured to a humeral head, according to an embodiment of the present disclosure.

As shown in FIG. 36, a plurality of holes 8134 such as threaded holes may be sized for receiving an adjustable thumbscrew 8600 (FIG. 34) engageable with, as shown in FIG. 37, one or more pins 8101 disposed in corresponding one of the plurality of through holes 8132 to secure the support 8100 to a humeral head 12.

Figure 38:
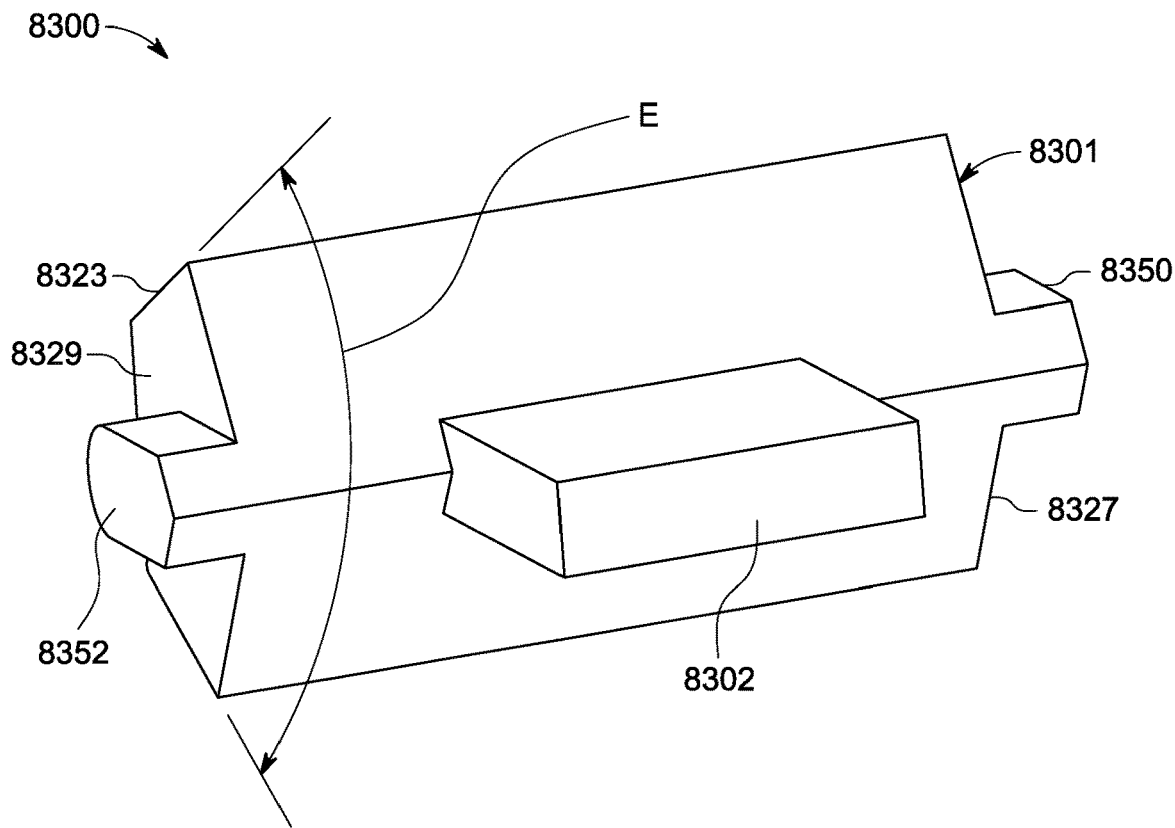
FIG. 38 is a top perspective view of the insert portion of the cutting guide system of FIG. 34, according to an embodiment of the present disclosure.
Figure 39:
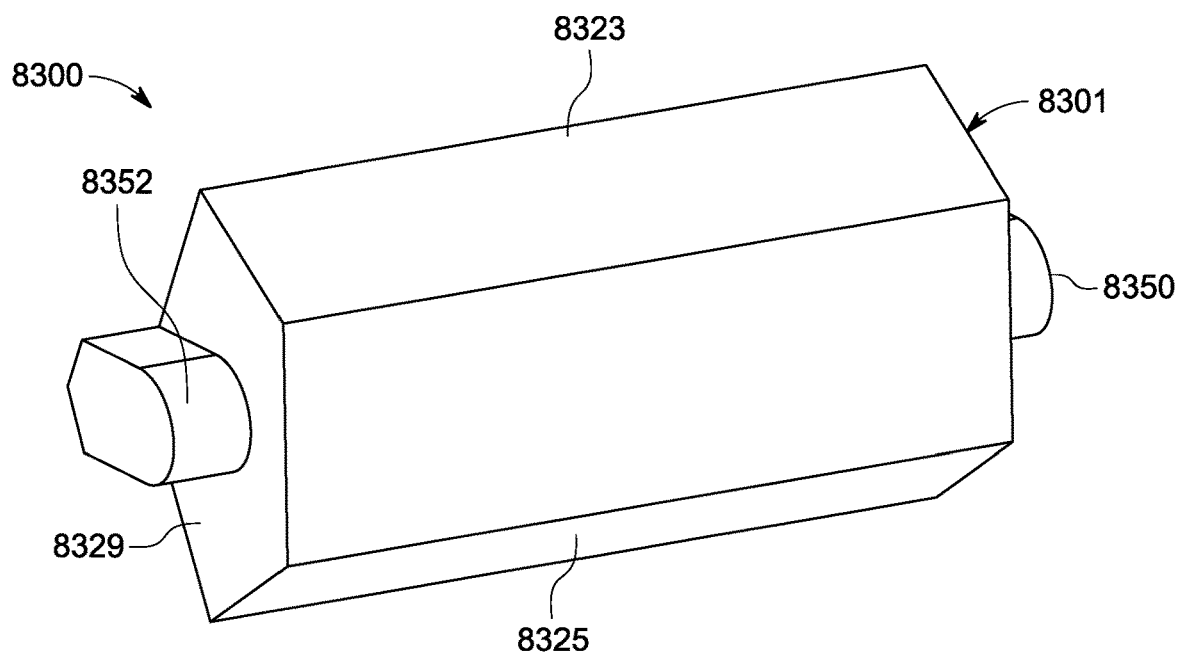
FIG. 39 is a bottom perspective view of the insert portion of the cutting guide system of FIG. 38, according to an embodiment of the present disclosure.

With reference to FIGS. 38 and 39, the insert portion 8300 may be operably sized and configured, and as shown in FIG. 34, disposable in the opening 8102 (FIG. 35) in the frame 8122 of the support portion 8100 for defining the first cutting slot 8500 and a second cutting slot 8550.

As shown in FIGS. 38 and 39, the insert portion 8300 may include a body 8301 having a first surface 8323, a second surface 8325, a third surface 8327, and a fourth surface 8329. The body 8301 may include an outwardly extending handle 8302 (FIG. 38). The third surface 8327 may be parallel to the fourth surface 8329. The third surface 8327 may include a first raised elongated projection 8350, and the fourth surface 8329 may include a second raised elongated projection 8352. The first surface 8323 is disposed at an angle relative to the second surface 8325. For example, the first surface 8323 of the body 8301 and the second surface 8325 of the body 8301 may be disposed at an angle E (FIG. 38) of between about 50 degrees and about 65 degrees. In some embodiments, the angle E (FIG. 38) may be between about 55 degrees and about 60 degrees, about 55 degrees, about 60 degrees, or other suitable angles.

Figure 40:
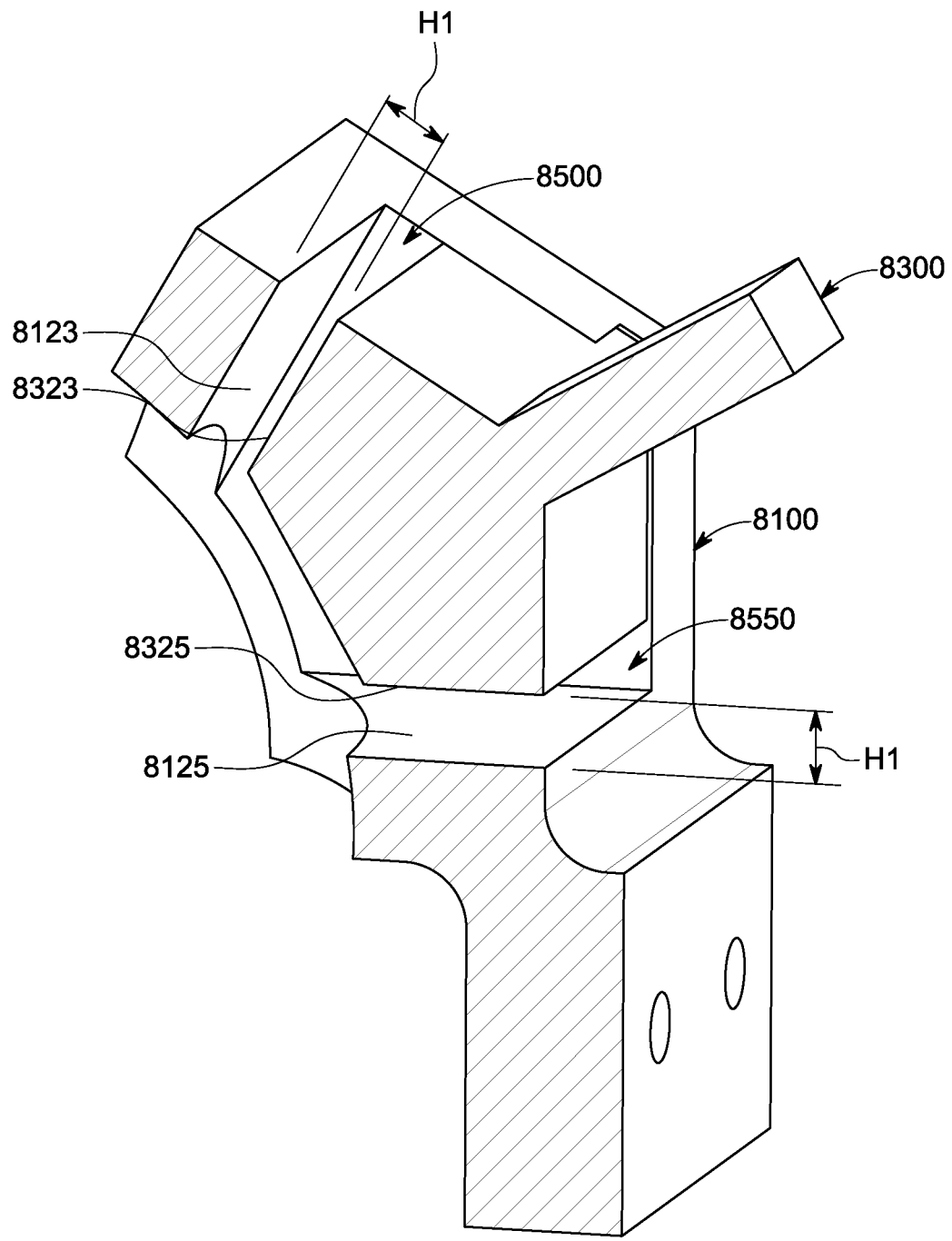
FIG. 40 is a cross-sectional view of the cutting guide system taken along line 40-40 in FIG. 34, according to an embodiment of the present disclosure.
Figure 41:
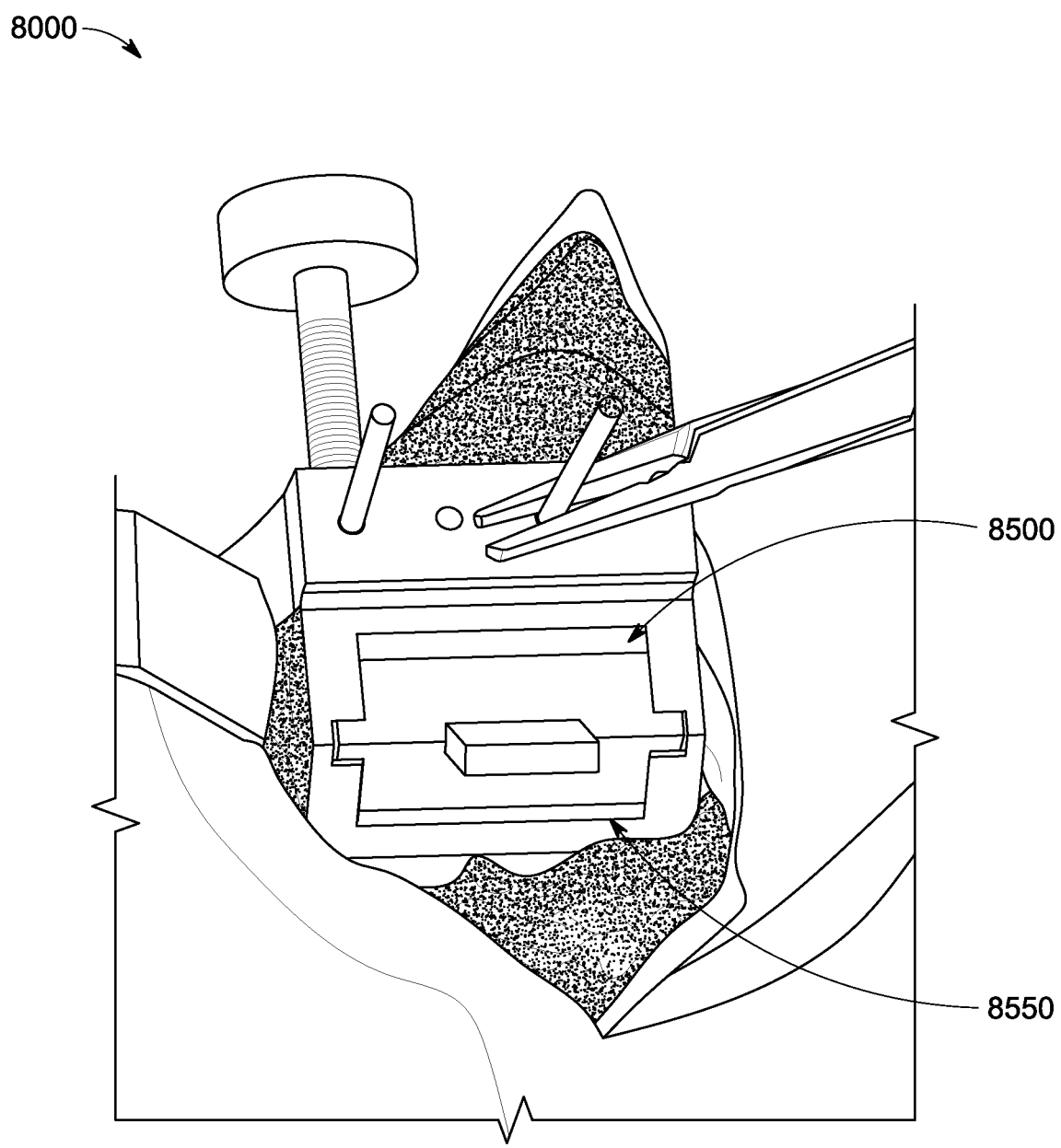
FIG. 41 is a perspective view of the cutting guide system of FIG. 34 secured to the humeral head prior to cutting the humeral head, according to an embodiment of the present disclosure.

With reference again to FIG. 34, the insert 8300 is positionable in the opening 8102 (FIG. 35) of the support portion 8100 by aligning and sliding the projections 8350 and 8352 of the insert 8300 into the recessed elongated channels 8150 and 8152, respectively, of the support portion. As shown in FIG. 40, the first surface 8323 of the insert portion 8300 and the first surface 8123 of the support portion 8100 define the first cutting guide or slot 8500 therebetween for resecting a first cut in a humeral head. The second surface 8325 of the insert portion 8300 and the second surface 8125 of the support portion 8100 define the second cutting guide or slot 8550 therebetween for resecting a second cut in a humeral head. The slot 8500 and the slot 8550 may be elongated slots having a width H1. FIG. 41 illustrates the cutting apparatus 8000 secured to a humeral head prior to resection of the humeral head.

Figure 42:
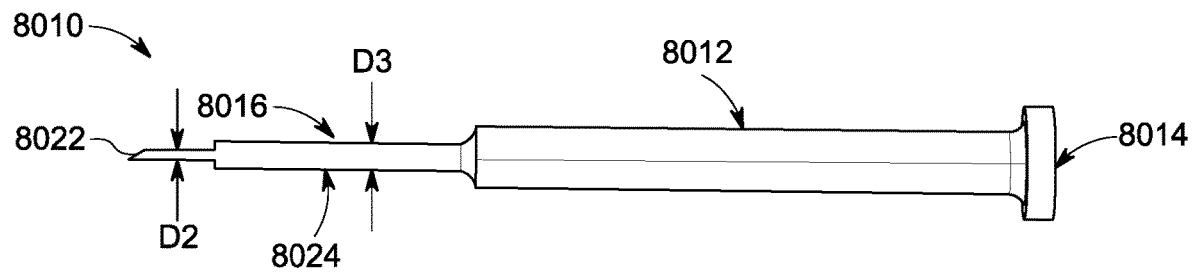
FIG. 42 is a side elevational view of a chisel, according to an embodiment of the present disclosure.

FIG. 42 illustrates a cutting tool or chisel 8010 having a body 8012 having a proximal portion 8014 and a distal portion 8016. The distal portion 8016 may include a cutting portion 8020 having a cutting edge 8022 and a stop portion 8024. For example, the cutting portion 8020 may be sized to pass through slots 8500 and 8550 (FIG. 34) of the cutting guide system 8000 (FIG. 34), while stop portion 8024 is sized to inhibit or limit the distance the cutting portion 8020 is extendable into the slot 8500 and the slot 8550 (FIG. 40). In some embodiments, the cutting portion 8020 may be cylindrical having a diameter D2 which is less than the distance H1 of the slots 8500 and 8550 (FIG. 40), and the stop portion 8024 may be cylindrical having a diameter D3, which is greater than the distance H1 of the slots 8500 and 8550 (FIG. 40).

Figure 43:
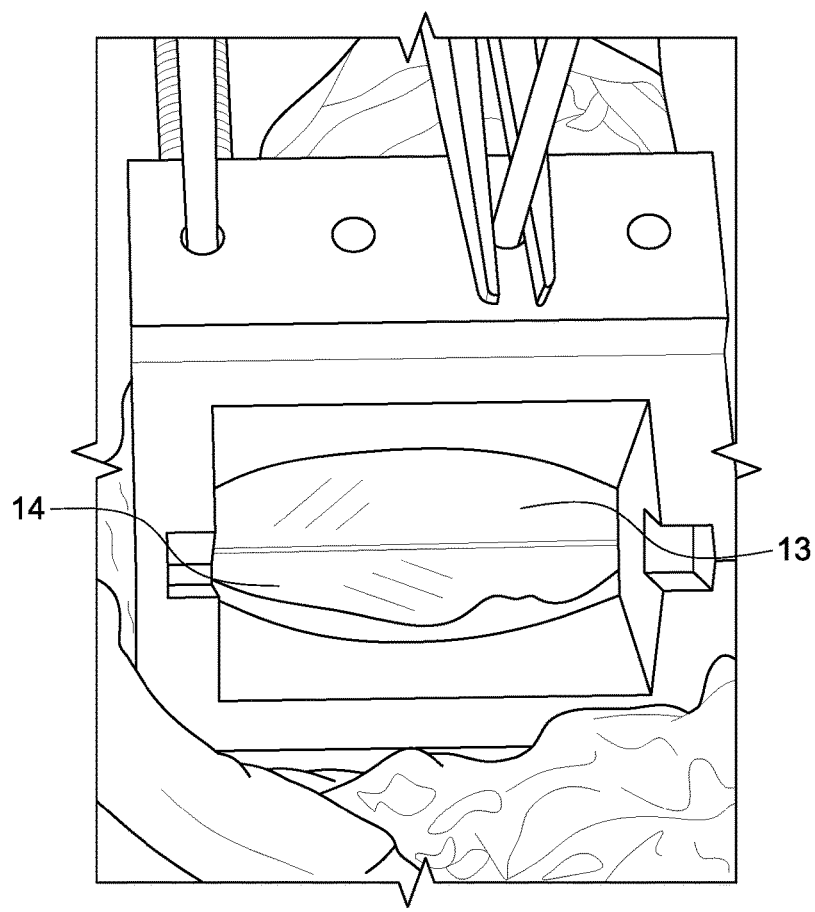
FIG. 43 is a perspective view of the support portion of FIG. 41 secured to the humeral head after forming a cutout in the humeral head and removing the insert portion, according to an embodiment of the present disclosure.

With reference again to FIG. 41, the cutting portion 8020 (FIG. 42) of the chisel 8010 (FIG. 42) may be inserted into the slot 8500 and the slot 8550 to form a first cut and a second cut in the humeral head, in which when the insert portion 8300 and the resected portion of the humeral head is removed, as shown in FIG. 43, the resected humeral head has a first cut surface 13 and a second cut surface 14. The cut in the humeral head may have the first and the second surfaces disposed at an angle of between about 50 degrees and about 65 degrees, about 55 degrees, about 60 degrees, or other suitable angles, to receive a wedge-shaped humeral implant.

In some embodiments, the cutting guide system 8000 may include the support portion being a one-piece, integral, or monolithic structure formed from a single material, and the insert portion being a one-piece, integral, or monolithic structure formed from a single material. The portions of the cutting guide system may be formed from plastic, stainless steel, or other suitable material or materials. In other embodiments, the portions of the cutting guide system may include multiple components. The pins may be Steinmann pins having a screw, chisel or trocar end for engaging the humeral head during the cutting of the humeral head around a lesion.

For example, the cutting guide system 8000 may be designed to fit onto the posterior half of the humeral head. The cutting guide system 8000 can be positioned over the lesion, then secured to the humerus using the pins. The cutting guide system 8000 allows the surgeon to resect the bone immediately around the lesion using either the chisel 8010 or an oscillating saw blade. The cutting guide system 8000 controls the depth and the width of the cut to ensure the correct fit of a corresponding selected implant or implant apparatus.

Figure 44:
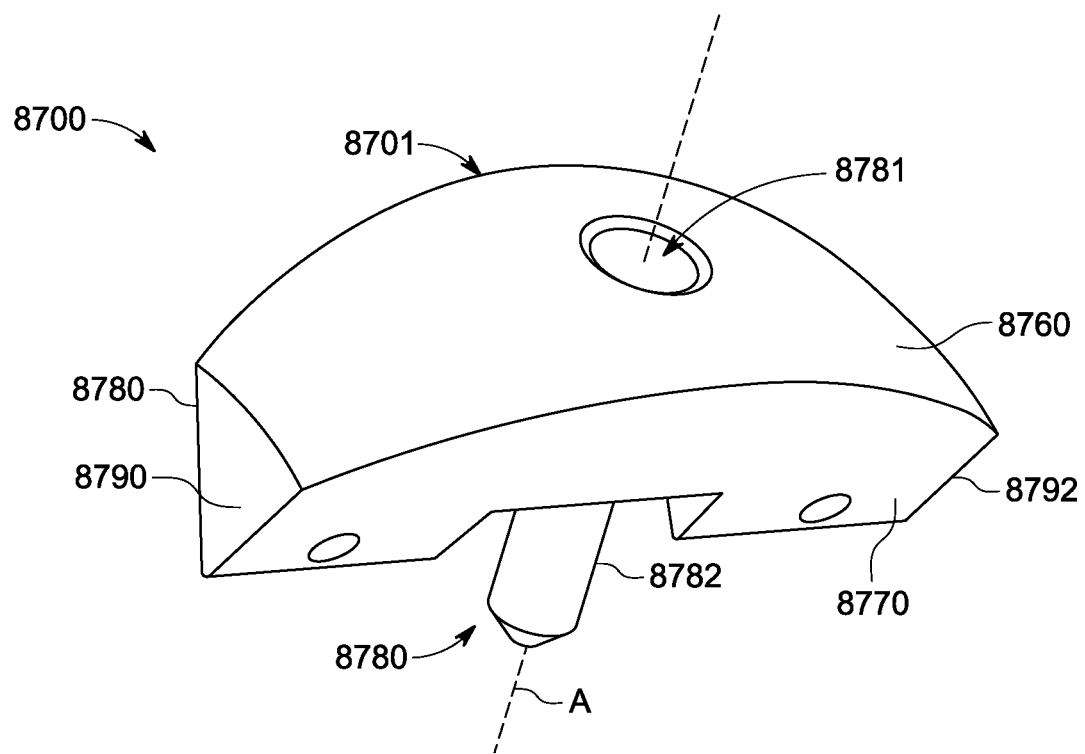
FIG. 44 is a perspective view of a humeral trial implant, according to an embodiment of the present disclosure.

FIG. 44 illustrates a trial implant 8700, according to an embodiment of the present disclosure. In this exemplary embodiment, the trial implant 8700 may include a body 8701 generally having a wedge geometry with shortened or truncated ends of the body. The size and shape of the trial implant 8700 may correspond to the size and shape, for example, of a corresponding humeral head implant.

For example, body 8701 may include a curved outer surface 8760, a first surface 8770, and a second surface 8780. The curved surface 8760 may be a generally convex surface that completes the articulating surface of the humeral head implant. The body 8701 may include shortened or truncated ends 8790 and 8792. The body 8710 includes a threaded opening 8781 extending into curved surface 8760. The intersecting edges of the first surface 8770 and the second surface 8780 may include a cutout 8780 having a post 8782 disposed therein which extends outwardly. For example, the threaded opening 8781 and the post 8782 may be axially aligned along an axis A. In some embodiments, the surface 8760 may have other configurations such as a flat surface or other shaped surface.

Figure 45:
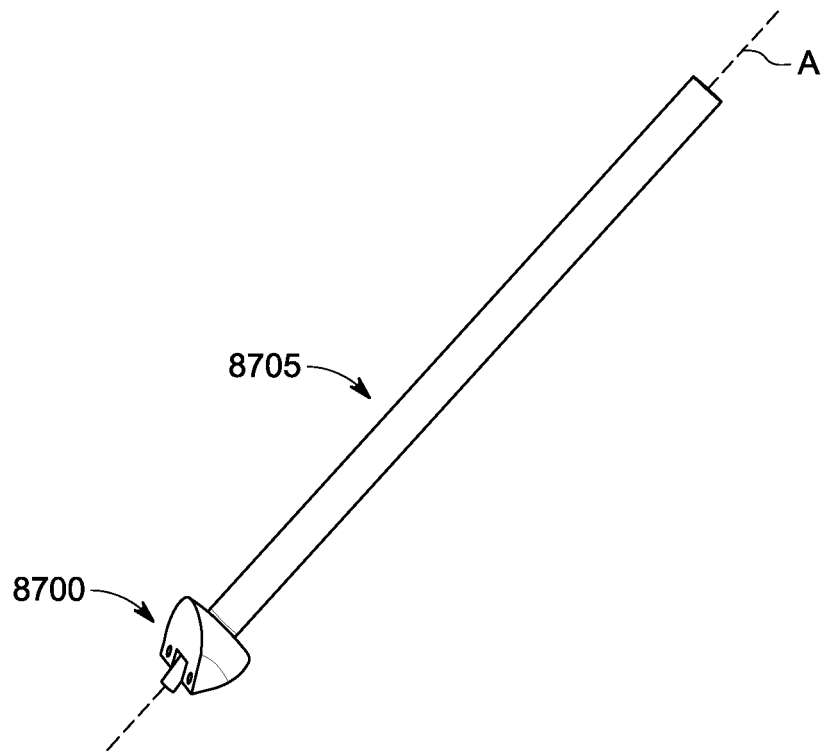
FIG. 45 is a perspective view of a humeral trial implant of FIG. 44 and a trial inserter, according to an embodiment of the present disclosure.

FIG. 45 illustrates a perspective view of the trial implant 8700 and a trial inserter 8705, according to an embodiment of the present disclosure. For example, the trial inserter 8705 includes an elongated body having a threaded end attachable to the threaded opening 8781 (FIG. 44) in the trial insert 8700 and aligned along the axis A. A surgeon can use the trial inserter 8705 to test, for example, the trial insert 8700 in a resected humeral head.

Figure 46:
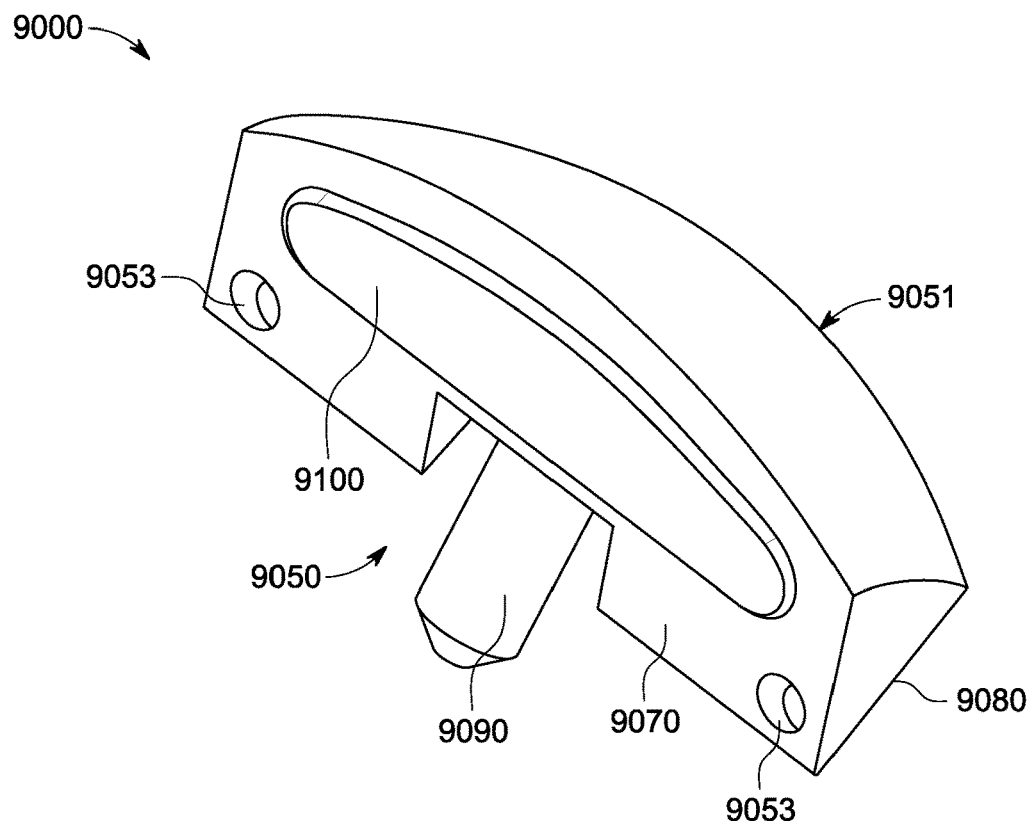
FIG. 46 is a perspective view of a humeral implant, according to an embodiment of the present disclosure.

FIG. 46 illustrates an implant apparatus 9000, according to an embodiment of the present disclosure. The implant apparatus 9000 may include a body 9051 that may be essentially the same as the body 5001 (FIG. 31) with the same wedge geometry having shortened or truncated ends of the body. For example, a first surface 9070 of body 9051 may include a raised portion 9100. The raised surface 9100 may be disposed in a first recess or relief (not shown) disposed generally in the center of first surface 9070. The first raised surface 9100 may be a first porous material layer.

The body 9051 may include a second surface 9080 having a second raised surface that is configured similar to the first surface having the first raised surface. The intersecting edges of the first surface 9070 and the second surface 9080 may include a cutout 9050 having a post 9090 disposed therein which extends outwardly. The post 9090 may be received in the hole or aperture formed by a corresponding post of a humeral trial implant in the resected humeral head. A plurality of through holes 9053 may extend from first surface 9070 to second surface 9080. Through holes 9053 may allow for supplemental fixation of the implant apparatus 9000 to, for example, a humeral head. For example, a suture (not shown) may be passed through one or more of the through holes and passed through a small tunnel in the humeral head to a suture button (not shown).

Figure 47:
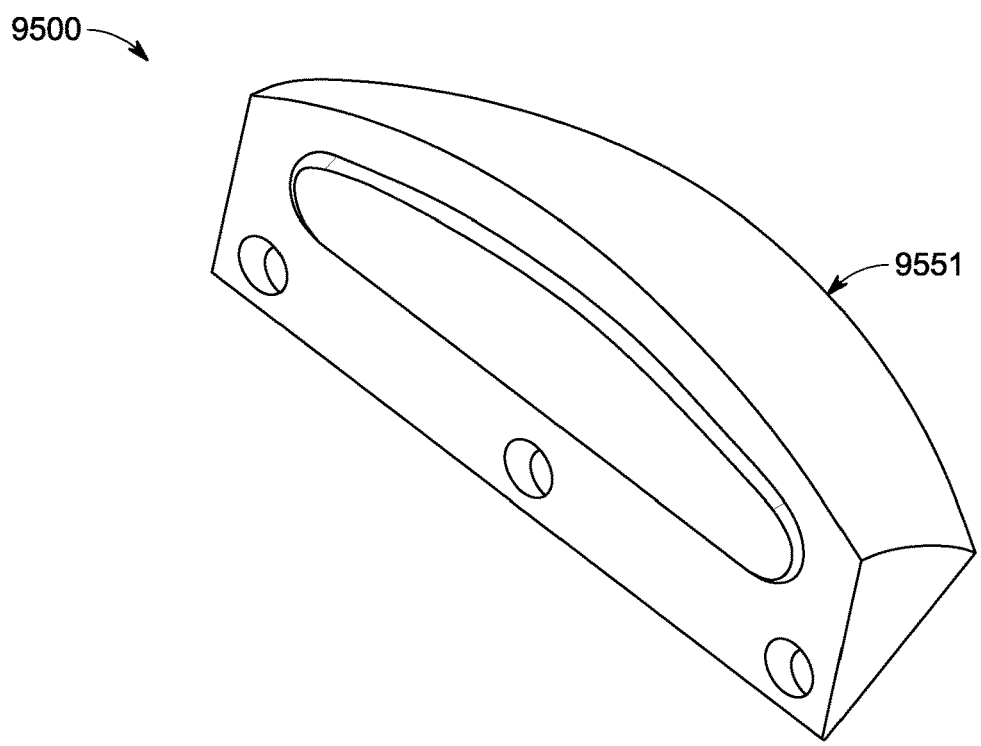
FIG. 47 is a perspective view of a humeral implant, according to an embodiment of the present disclosure.

FIG. 47 illustrates an implant 9500, according to an embodiment of the present disclosure. The implant 9500 may include a body 9551 that may be essentially the same as the body 5001 (FIG. 31) with the same wedge geometry having shortened or truncated ends of the body, and with the exception of not including an outwardly extending post.

Figure 48:
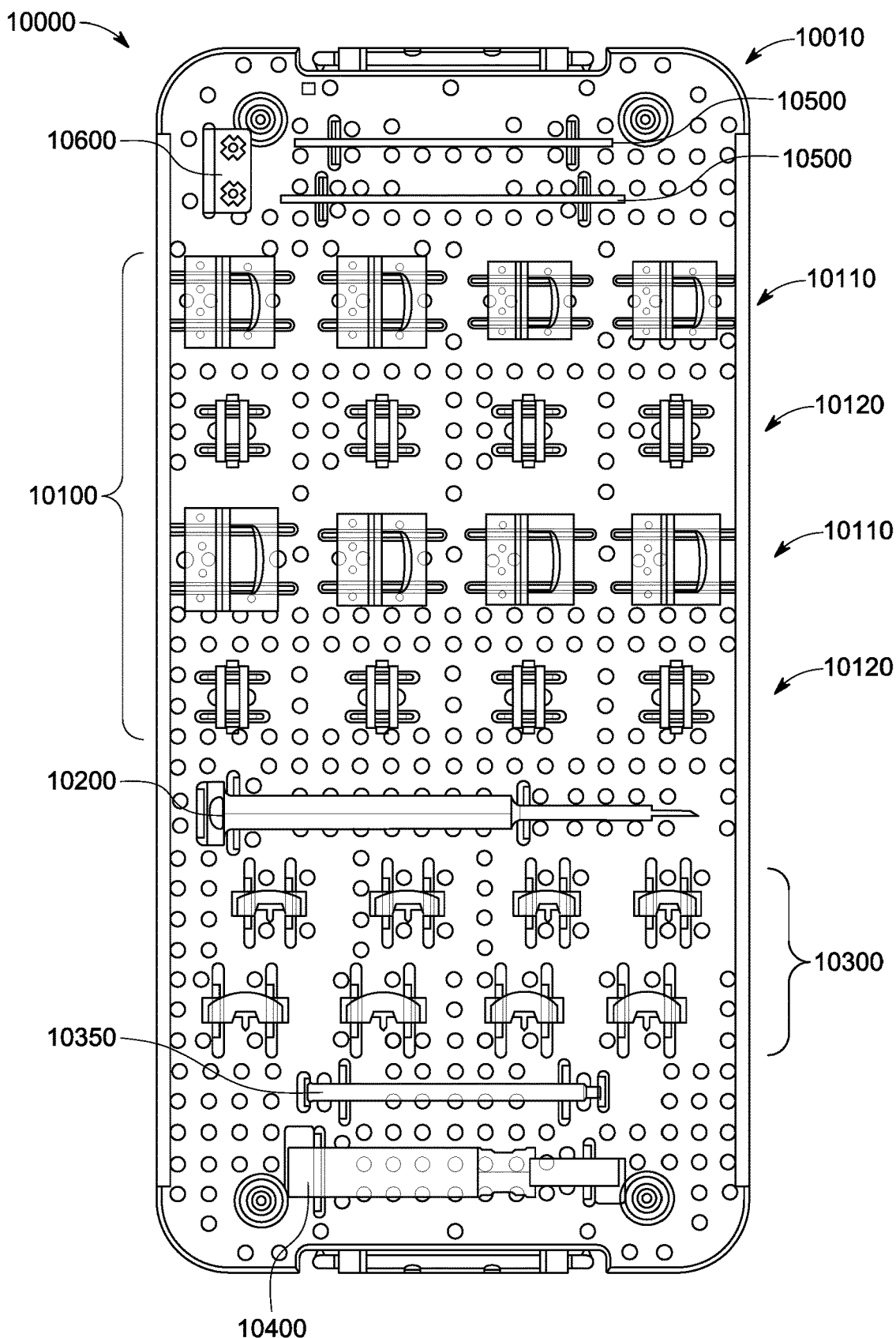
FIG. 48 is a plan view of a humeral cutting guide system and humeral trial implant kit, according to an embodiment of the present disclosure.

FIG. 48 illustrates a cutting guide system and trial implant kit 10000, according to an embodiment of the present disclosure. In this illustrated kit 10000, the kit 10000 may include a housing or case 10010, a plurality of differently sized implant cutting systems 10100 including a plurality of support inserts 10110 and a plurality of insert portions 10120, a chisel 10200, a plurality trial implants 10300, an insert handle 10350, an impactor 10400, a radius guide 1050, and thumbscrews 10600. In some embodiments, the cut guides and the trial implants may include 8 different sizes and/or configurations for repair of a humeral head. For example, the sizes and/or configurations may include a radius 28 mm large, a radius 26 mm large, a radius 23 mm large, a radius 20 mm large, a radius 28 mm small, a radius 26 mm small, a radius 23 mm small, a radius 20 mm small, a radius 28 mm small, and other suitable sizes and/or configurations.

Benefits of the present disclosure include efficiently providing a repair of a Hill-Sachs lesions in a humeral head that may allow for greater range of motion compared to remplissage procedures. Further benefits of the present disclosure may include shorter surgery time (no need to prepare allograft), and minimal bone resection as the implant or implant apparatus is selected based on the lesions being repaired). From the present description, the technique of the present disclosure may be applicable to other bones in the body of a patient.

As may be recognized by those of ordinary skill in the art based on the teachings herein, numerous changes and modifications may be made to the above-described and other embodiments of the present invention without departing from the scope of the invention. The implants, screws, and other components of the devices and/or apparatus as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the devices and apparatus may include more or fewer components or features than the embodiments as described and illustrated herein. Accordingly, this detailed description of the currently-preferred embodiments is to be taken as illustrative, as opposed to limiting the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general apparatus operation. Modifications and alterations will occur to others upon a reading and understanding of the preceding detailed description. It is intended that the invention be construed as including all such modifications and alterations.

The invention claimed is:

1. A humeral implant system comprising:
    an implant comprising a spherical wedge comprising:
        an elongated convex upper surface with a first edge and a spaced apart second edge, said first edge tapering towards said second edge at one end of the elongated convex upper surface and said first edge tapering towards said second edge at an opposite end of said elongated convex upper surface so that the elongated convex upper surface is wider in the middle and narrower at the distal ends;
        a first surface having a curved upper edge joined to said first edge of said elongated convex upper surface, the first surface comprising an elongated planar surface;
        a second surface having a curved upper edge joined to said second edge of said elongated convex upper surface, the second surface comprising an elongated planar surface;
        a lower elongated straight edge of said first surface is joined to a lower edge of said second surface; and
        wherein said first surface and said second surface are disposed at an angle with said first surface and said second surface tapering from said convex upper surface towards each other to said lower elongated straight edge; and
    a cutting system having a body with a first guide and a second guide for resecting a cutout in a humeral head, the cutout having a first surface and a second surface corresponding to said first surface and said second surface of said implant.

2. The humeral implant system of claim 1, wherein said implant comprises a first porous material disposed on said first surface of said implant, and a second porous material disposed on said second surface of said implant.

3. The humeral implant system of claim 2, wherein said first surface of said implant comprises a first relief, said second surface of said implant comprises a second relief, and wherein said first porous material is disposed in said first relief, and said second porous material is disposed in said second relief.

4. The humeral implant system of claim 3, wherein said first relief comprises a tapered first relief, said second relief comprises a tapered second relief, said first porous material comprises a constant thickness porous material, and said second porous material comprises a constant thickness porous material.

5. The humeral implant system of claim 4, wherein said first porous material comprises an arcuate shape, and said second porous material comprises an arcuate shape.

6. The humeral implant system of claim 1, wherein said first surface of said implant comprises at least one outwardly extending first projection, and said second surface of said implant comprises at least one outwardly extending second projection.

7. The humeral implant system of claim 1, wherein said implant comprises said spherical wedge having truncated ends.

8. The humeral implant system of claim 1, wherein said implant comprises a metal and/or polymeric material.

9. The humeral implant system of claim 1, wherein said body of said cutting system comprises an inner curved surface disposable towards the humeral head.

10. The humeral implant system of claim 9, wherein said body of said cutting system comprises a plurality of through holes for receiving pins for use in operably connecting said cutting system to the humeral head.

11. The humeral implant system of claim 1, wherein the cutting system comprises a frame having an opening extending therethrough, and an insert disposable in said opening in said frame, said frame and said insert defining a first cutting slot and a second cutting slot.

12. The humeral implant system of claim 11, wherein said first inside surface of said frame and said second inside surface of said frame are disposed at an angle of between 50 degrees and 65 degrees.

13. The humeral implant system of claim 11, wherein said first inside surface of said frame and said second inside surface of said frame are disposed at an angle of 55 degrees or 60 degrees.

14. The humeral implant system of claim 11, wherein said frame defines a concave surface extendable towards the humeral head.

15. The humeral implant system of claim 11, further comprising a plurality of differently sized humeral implant cutting systems, a plurality of differently sized humeral trial implants, and at least one cutting tool.

16. The humeral implant system of claim 1, wherein said cutting system comprises a drill guide, a cutting support, and a milling guide.

17. An implant system comprising:
    an implant comprising a spherical wedge comprising:
        an elongated curved upper surface with a first edge and a spaced apart second edge, said first edge tapering towards said second edge at one end of the elongated convex upper surface, and said first edge tapering towards said second edge at an opposite end of said elongated convex upper surface so that the elongated convex upper surface is wider in the middle and narrower at the distal ends;

a first surface having a curved upper edge joined to said first edge of said elongated curved upper surface, the first surface comprising an elongated planar surface;

a second surface having a curved upper edge joined to said second edge of said elongated curved upper surface, the second surface comprising an elongated planar surface;

a lower elongated straight edge of said first surface is joined to a lower edge of said second surface; and wherein said first surface and said second surface are disposed at an angle with said first surface and said second surface tapering from said convex upper surface towards each other to said lower elongated straight edge; and a cutting system having a body with a first guide and a second guide for resecting a cutout in a bone of a patient, the cutout having a first surface and a second surface corresponding to said first surface and said second surface of said implant.

18. The implant system of claim 17, wherein said implant comprises a first porous material disposed on said first surface of said implant, and a second porous material disposed on said second surface of said implant.

19. The implant system of claim 18, wherein said first surface of said implant comprises a first relief, said second surface of said implant comprises a second relief, and wherein said first porous material is disposed in said first relief, and said second porous material is disposed in said second relief.

20. The implant system of claim 19, wherein said first relief comprises a tapered first relief, said second relief comprises a tapered second relief, said first porous material comprises a constant thickness porous material, and said second porous material comprises a constant thickness porous material.

21. The implant system of claim 20, wherein said first porous material comprises an arcuate shape, and said second porous material comprises an arcuate shape.

22. The implant system of claim 17, wherein said implant comprises a metal and/or polymeric material.

23. The implant system of claim 17, wherein said body of said cutting system comprises an inner curved surface disposable towards the bone of the patient.

24. The implant system of claim 17, wherein said body of said cutting system comprises a plurality of through holes for receiving pins for use in operably connecting said cutting system to the bone of the patient.

25. The implant system of claim 17, wherein the cutting system comprises a frame having an opening extending therethrough, and an insert disposable in said opening in said frame, said frame and said insert defining a first cutting slot and a second cutting slot.

26. The implant system of claim 25, wherein said first inside surface of said frame and said second inside surface of said frame are disposed at an angle of between 50 degrees and 65 degrees.

27. The implant system of claim 25, wherein said first inside surface of said frame and said second inside surface of said frame are disposed at an angle of 55 degrees or 60 degrees.

28. The implant system of claim 25, wherein said frame defines a concave surface extendable towards the bone of the patient.

29. The implant system of claim 17, further comprising a plurality of differently sized implant cutting systems, a plurality of differently sized trial implants, and at least one cutting tool.

30. The implant system of claim 17, wherein said cutting system comprises a drill guide, a cutting support, and a milling guide.

* * * * *